US009492541B2

(12) United States Patent
Srinivasan et al.

(10) Patent No.: US 9,492,541 B2
(45) Date of Patent: *Nov. 15, 2016

(54) PHENYLEPHERINE CONTAINING DOSAGE FORM

(75) Inventors: Viswanathan Srinivasan, The Woodlands, TX (US); Ralph Brown, Southlake, TX (US); David Brown, Colleyville, TX (US); Juan Carlos Menendez, Bedford, TX (US); Venkatesh Balasubramanian, Arlington, TX (US); Somphet Peter Suphasawud, Fort Worth, TX (US)

(73) Assignee: SOVEREIGN PHARMACEUTICALS, LLC, Fort Worth, TX (US)

( * ) Notice: Subject to any disclaimer, the term of this patent is extended or adjusted under 35 U.S.C. 154(b) by 2648 days.

This patent is subject to a terminal disclaimer.

(21) Appl. No.: 10/939,351

(22) Filed: Sep. 14, 2004

(65) Prior Publication Data

US 2006/0057205 A1 Mar. 16, 2006

(51) Int. Cl.
| | |
|---|---|
| A61K 9/20 | (2006.01) |
| A61K 31/137 | (2006.01) |
| A61K 45/06 | (2006.01) |
| A61K 9/24 | (2006.01) |
| A61K 31/485 | (2006.01) |

(52) U.S. Cl.
CPC ............ *A61K 45/06* (2013.01); *A61K 9/209* (2013.01); *A61K 31/137* (2013.01); *A61K 31/485* (2013.01)

(58) Field of Classification Search
USPC ........................ 424/464, 468, 472
See application file for complete search history.

(56) References Cited

U.S. PATENT DOCUMENTS

| | | | |
|---|---|---|---|
| 4,294,820 A | | 10/1981 | Keith et al. |
| 4,389,393 A | | 6/1983 | Schor et al. |
| 4,631,284 A | | 12/1986 | Salpekar et al. |
| 4,650,807 A | * | 3/1987 | Findlay et al. ............... 514/343 |
| 4,792,448 A | | 12/1988 | Ranade |
| 4,820,523 A | * | 4/1989 | Shtohryn et al. ............ 424/469 |
| 4,839,354 A | * | 6/1989 | Sunshine et al. .......... 514/226.5 |
| 4,882,158 A | | 11/1989 | Yang et al. |
| 5,032,401 A | | 7/1991 | Jamas et al. |
| 5,133,974 A | | 7/1992 | Paradissis et al. |
| 5,445,829 A | | 8/1995 | Paradissis et al. |
| 5,840,731 A | * | 11/1998 | Mayer et al. .................. 514/289 |
| 6,001,392 A | * | 12/1999 | Wen et al. ..................... 424/486 |
| 6,287,597 B1 | | 9/2001 | Gordziel |
| 6,372,254 B1 | | 4/2002 | Ting et al. |
| 6,462,094 B1 | | 10/2002 | Dang et al. |
| 6,602,521 B1 | | 8/2003 | Ting et al. |
| 6,699,502 B1 | | 3/2004 | Fanara et al. |
| 6,797,283 B1 | | 9/2004 | Edgren et al. |
| 2004/0220153 A1 | | 11/2004 | Jost-Price et al. |
| 2004/0229849 A1 | | 11/2004 | Jost-Price et al. |
| 2004/0253311 A1 | | 12/2004 | Berlin et al. |
| 2005/0112199 A1 | | 5/2005 | Padval et al. |
| 2005/0152967 A1 | | 7/2005 | Tengler et al. |
| 2005/0153947 A1 | | 7/2005 | Padval et al. |

OTHER PUBLICATIONS

U.S. Appl. No. 10/736,902, filed Dec. 17, 2003 and entitled "Dosage Form Containing Promethazine and Another Drug".
U.S. Appl. No. 10/798,884, filed Mar. 12, 2004 and entitled "Dosage Form Containing a Morphine Derivative and Another Drug".
U.S. Appl. No. 10/910,806, filed Aug. 4, 2004 and entitled "Dosage Form Containing Carbetapentane and Another Drug".
U.S. Appl. No. 11/012,267, filed Dec. 16, 2004 and entitled "Dosage Form Containing Diphenhydramine and Another Drug".
U.S. Appl. No. 11/102,725, filed Apr. 11, 2005 and entitled "Promethazine Containing Dosage Form".
U.S. Appl. No. 11/102,726, filed Apr. 11, 2005 and entitled "Diphenhydramine Containing Dosage Form".
U.S. Appl. No. 11/115,321, filed Apr. 27, 2005 and entitled "Dosage Form Containing Multiple Drugs".
U.S. Appl. No. 11/115,293, filed Apr. 27, 2005 and entitled "Dosage Form Containing Promethazine and Another Drug".

* cited by examiner

*Primary Examiner* — Jessica Worsham
(74) *Attorney, Agent, or Firm* — Abel Law Group, LLP

(57) ABSTRACT

A pharmaceutical dosage form which comprises phenylepherine or a pharmaceutically acceptable salt thereof and a second drug. The dosage form provides a plasma concentration within the therapeutic range of the second drug over a period which is coextensive with at least about 70% of the period over which the dosage form provides a plasma concentration within the therapeutic range of phenylepherine. This abstract is neither intended to define the invention disclosed in this specification nor intended to limit the scope of the invention in any way.

112 Claims, No Drawings

PHENYLEPHERINE CONTAINING DOSAGE FORM

FIELD OF THE INVENTION

The present invention relates to a pharmaceutical dosage form which contains phenylepherine and/or a pharmaceutically acceptable salt thereof in combination with at least one additional active ingredient. The dosage form releases phenylepherine and the additional active ingredient at rates which provide pharmaceutically suitable plasma concentrations of all the active pharmaceutical ingredients over similar periods of time. The present invention also relates to a process for manufacturing the dosage form and to methods for alleviating nasal and respiratory congestion in human subjects with the oral administration of phenylepherine and of ameliorating associated conditions such as excessive coughing, watery nasal passages, weeping eyes, sinus congestion and pain, headache, joint pain, bronchitis, and thick tenacious mucus exudates that inhibit nasal breathing and irritate the throat.

Still further, the present invention relates to the administration of phenylepherine and/or a pharmaceutically acceptable salt thereof in higher amounts (in particular, per time unit) than has previously been considered expedient from a pharmaceutical and medical point of view.

DISCUSSION OF BACKGROUND INFORMATION

Phenylepherine, when taken orally by human subjects in adequate dosages (usually in the form of phenylepherine hydrochloride or any other pharmaceutically acceptable salt of phenylepherine), relieves swelling of the mucous membranes of the nose and contiguous respiratory mucosa when this swelling is caused by viral or allergic conditions. It thereby helps restore normal breathing and—by preventing mouth breathing—aids in the restoration of normal ciliary activity in the nasal mucosa which permits draining of retained secretions. However, congestion of the respiratory mucosa is usually accompanied by conditions such as histamine release, excessive coughing, headache, joint pain, and thick tenacious mucus exudates for which antihistamines, pain relieving medication, expectorants, mucus thinning drugs, cough suppressants and other agents are indicated.

However, a single dose of phenylepherine or a pharmaceutically acceptable salt thereof provides a therapeutically effective plasma concentration for 2.5±0.7 hours whereas many agents used in conjunction with phenylepherine provide effective plasma concentrations that differ markedly from this therapeutic profile.

For example, a single dose of an immediate release expectorant such as guaifenesin will usually provide relief for only about one hour, and pain relieving agents and many antihistamines usually provide relief for about 4 to 8 hours per single dose. As a result, there appears to be virtually no benefit in combining phenylepherine with any drug with a noticeably shorter or longer effective period in a single dosage form. Depending on the therapeutic levels attained with the drug used in conjunction with phenylepherine, the phenylepherine will provide the desired therapeutic effect when the other drug has either ceased to be effective, or continues to exert a therapeutic effect which prohibits administration of another dose even though the decongestant effect of phenylepherine has ceased.

It would be desirable if patients suffering from, e.g., respiratory congestion, for which phenylepherine is indicated, would also obtain relief of accompanying symptoms such as excessive coughing, inflammation of the respiratory mucosa and sinus cavities, weeping eyes, bronchitis, rhinitis, rhinorrhea, Eustachian Tube congestion, nausea, headache and joint pain, over a similar time period, by administering a single dose of a dosage form such as, e.g., a tablet, liquid, syrup, suspension, capsule and the like which provides both phenylepherine and one or more other drugs that permits release of the drugs from separate release matrices which are individually formulated for each ingredient's therapeutic profile.

Further, the advent of sustained-release granulation technology has made it possible to achieve and maintain therapeutic levels of a drug at a pre-determined rate, limited only by the normal transit time of orally ingested products through the human alimentary canal. Although this technology has been used to provide sustained-release levels of phenylepherine, the developers of these products have failed to develop a sustained-release or timed-release formulation that provides consistent therapeutic levels of this pharmaceutical agent throughout the dosage periods indicated in the labeling. This failure is evident by the dosages of the products available. These dosages range from 30 to 40 milligrams every 12 hours for an orally ingested sustained-release tablet.

It would be desirable to administer a dosage form, in particular, a sustained-release dosage form, of phenylepherine or a pharmaceutically acceptable salt thereof in better conformity and agreement with the plasma half-life of phenylepherine (2 to 2.5 hours in humans) and the immediate release dosage level of phenylepherine hydrochloride of 10 milligrams every 4 to 6 hours for a daily maximum of 60 mg which is recognized as effective in adults by the United States Food and Drug Administration.

SUMMARY OF THE INVENTION

The present invention provides a pharmaceutical dosage form which comprises a first drug which is selected from phenylepherine and pharmaceutically acceptable salts thereof and at least one second drug. This dosage form provides a plasma concentration within the therapeutic range of the at least one second drug over a period which is coextensive with at least about 70% of the period over which the dosage form provides a plasma concentration within the therapeutic range of phenylepherine.

In one aspect, the first drug may comprise one or more pharmaceutically acceptable salts of phenylepherine. Preferably, the first drug comprises at least phenylepherine hydrochloride.

In another aspect, the at least one second drug may comprise one or more of an expectorant, a mucus thinning drug, an antihistamine, an antitussive drug and an analgesic.

In yet another aspect, the at least one second drug may comprise an antitussive drug. By way of non-limiting example, the at least one second drug may comprise one or more of codeine, hydrocodone, dihydrocodeine and carbetapentane, as such and/or in the form of pharmaceutically acceptable salts thereof. Non-limiting examples of the latter salts include codeine phosphate, hydrocodone bitartrate, dihydrocodeine bitartrate and carbetapentane citrate.

In yet another aspect, the at least one second drug may comprise one or more antihistamines. Non-limiting examples of suitable antihistamines comprise astemizole, zatadine, bromodiphenhydramine, brompheniramine, carbinoxamine, cetirizine, chlorcyclizine, clemastine, chlorothen, chlorpheniramine, cyclizine, cyproheptadine, desloratadine, dimethindene, diphenhydramine, diphenylpyraline, doxylamine, fexofenadine, hydroxyine, isothipendyl, loratadine, methapyrilene, montelukast, phenindamine, pheniramine, phenyltoloxamine, promethazine, prophenpyridamine, pyrilamine, terfenadine, thenyldiamine, thonzylamine, trimeprazine, tripelennamine, triprolidine, and pharmaceutically acceptable salts thereof such as, e.g., zatadine maleate, bromodiphenhydramine HCl, brompheniramine maleate, carbinoxamine maleate, cetirizine HCl, chlorcyclizine HCl, clemastine fumarate, chlorothen citrate, chlorpheniramine maleate, dimethindene maleate, diphenhydramine HCl, fexofenadine HCl, hydroxyine HCl, isothipendyl HCl (theruhistin), methapyrilene fumarate, methapyrilene HCl, montelukast sodium, phenindamine tartrate, pheniramine maleate, phenyltoloxamine citrate, promethazine hydrochloride, prophenpyridamine maleate, pyrilamine maleate, thenyldiamine HCl, trimeprazine tartrate, tripelennamine HCl and triprolidine HCl.

In a still further aspect, the at least one second drug may comprise one or more expectorants. A non-limiting example of a preferred expectorant for use in the present invention is guaifenesin.

In another aspect of the dosage form of the present invention, the plasma half-life of the at least one second drug may differ from the plasma half-life of phenylepherine by at least about 2 hours, e.g., by at least about 3 hours, or by at least about 4 hours (or even by at least about 5 hours, at least about 6 hours, at least about 7 hours, at least about 8 hours, at least about 10 hours or at least about 12 hours).

In yet another aspect of the present dosage form, the period of the plasma concentration within the therapeutic range of the at least one second drug may be coextensive with at least about 80%, e.g., at least about 90%, or at least about 95% of the period of a plasma concentration within the therapeutic range of phenylepherine.

In a still further aspect of the dosage form of the present invention, the dosage form may comprise a tablet. This tablet may, for example, comprise at least two layers, such as a bi-layered tablet. Alternatively or additionally, the tablet may comprise a matrix which comprises one of the first drug and the at least one second drug and has dispersed therein particles which comprise the other one of the first drug and the at least one second drug.

In yet another aspect, the dosage form may comprise a solution or a suspension.

The present invention also provides a bi-layered tablet which comprises a first layer and a second layer. The first layer comprises a first drug which is selected from phenylepherine and pharmaceutically acceptable salts thereof. The second layer comprises at least one second drug which is selected from antitussives, expectorants, mucus thinning drugs, analgesics, and antihistamines. This bi-layered tablet provides a plasma concentration within the therapeutic range of the at least one second drug over a period which is coextensive with at least about 70% of the period over which the bi-layered tablet provides a plasma concentration within the therapeutic range of phenylepherine.

In one aspect of the bi-layered tablet, the first layer may comprise phenylepherine hydrochloride and/or phenylepherine tannate.

In another aspect of the bi-layered tablet, the second layer may comprises one or more of dextromethorphan, carbetapentane, codeine, dihydrocodeine, hydrocodone, guaifenesin, astemizole, azatadine, bromodiphenhydramine, brompheniramine, carbinoxamine, cetirizine, chlorcyclizine, chlorpheniramine, clemastine, chlorothen, cyclizine, cyproheptadine, desloratadine, dimethindene, diphenhydramine, diphenylpyraline, doxylamine, fexofenadine, hydroxyine, isothipendyl, loratadine, methapyrilene, methapyrilene, montelukast, phenindamine, pheniramine, phenyltoloxamine, promethazine, prophenpyridamine, pyrilamine, thonzylamine, thenyldiamine, trimeprazine, tripelennamine, triprolidine, acetaminophen, ibuprofen, and pharmaceutically acceptable salts of these compounds, such as, e.g., dextromethorphan hydrobromide, carbetapentane citrate, codeine phosphate, dihydrocodeine bitartrate, hydrocodone bitartrate, guaifenesin HBr, azatadine maleate, bromodiphenhydramine HCl, brompheniramine maleate, carbinoxamine maleate, cetirizine HCl, chlorcyclizine HCl, chlorpheniramine maleate, clemastine fumarate, chlorothen citrate, dimethindene maleate, diphenhydramine HCl, fexofenadine HCl, hydroxyine HCl, isothipendyl HCl (theruhistin), methapyrilene fumarate, methapyrilene HCl, montelukast sodium, phenindamine tartrate, pheniramine maleate, phenyltoloxamine citrate, promethazine HCl, prophenpyridamine maleate, pyrilamine maleate, thenyldiamine HCl, trimeprazine tartrate, tripelennamine HCl, and triprolidine HCl.

In yet another aspect, the bi-layered tablet may comprise at least two of dextromethorphan hydrobromide, carbetapentane citrate, codeine phosphate, dihydrocodeine bitartrate, hydrocodone bitartrate, guaifenesin HBr, astemizole, azatadine maleate, bromodiphenhydramine HCl, brompheniramine maleate, carbinoxamine maleate, cetirizine HCl, chlorcyclizine HCl, chlorpheniramine maleate, clemastine fumarate, chlorothen citrate, cyclizine, cyproheptadine, desloratadine, dimethindene maleate, diphenhydramine HCl, diphenylpyraline, doxylamine, fexofenadine HCl, hydroxyine HCl, isothipendyl HCl (theruhistin), loratadine, methapyrilene fumarate, methapyrilene HCl, montelukast sodium, phenindamine tartrate, pheniramine maleate, phenyltoloxamine citrate, promethazine HCl, prophenpyridamine maleate, pyrilamine maleate, terfenadine, thenyldiamine HCl, thonzylamine, trimeprazine tartrate, tripelennamine HCl, triprolidine HCl, acetaminophen and ibuprofen.

In another aspect of the bi-layered tablet, the first layer thereof may comprise the first drug as the only active ingredient in the first layer.

In a still further aspect, the period of a plasma concentration within the therapeutic range of the at least one second drug may be coextensive with at least about 80%, e.g., at least about 90%, of the period of a plasma concentration within the therapeutic range of phenylepherine.

In yet another aspect of the bi-layered tablet, one of the first and second layers may be an immediate release layer. For example, the first layer may be an immediate release layer, or the second layer may be an immediate release layer. In another aspect, the first and second layers may both be controlled release layers.

In another aspect, the bi-layered tablet may comprise a total of from about 1 mg to about 100 mg of phenylepherine or an equivalent amount of at least one pharmaceutically acceptable salt of phenylepherine, for example, a total of from about 10 mg to about 75 mg.

In yet another aspect, the bi-layered tablet may comprise (i) from about 0.1 mg to about 16 mg of chlorpheniramine maleate or an equivalent amount of at least one other pharmaceutically acceptable salt of chlorpheniramine; and/or (ii) about 0.1 mg to about 120 mg of one or more of codeine, dihydrocodeine, hydrocodone and pharmaceutically acceptable salts thereof; and/or (iii) from about 1 mg to about 240 mg of diphenhydramine hydrochloride or an equivalent amount of at least one other pharmaceutically acceptable salt of diphenhydramine; and/or (iv) from about 0.1 mg to about 75 mg of promethazine hydrochloride or an equivalent amount of at least one other pharmaceutically acceptable salt of promethazine; and/or (v) from about 0.1 mg to about 32 mg of carbinoxamine maleate or an equivalent amount of at least one other pharmaceutically acceptable salt of carbinoxamine; and/or (vi) from about 1 mg to about 2400 mg of guaifenesin.

In a still further aspect, the first layer of the bi-layered tablet of the present invention may comprise from about 1 mg to about 75 mg of phenylepherine or an equivalent amount of at least one pharmaceutically acceptable salt of phenylepherine, and at least one of (i) from about 1 mg to about 75 mg of codeine phosphate or an equivalent amount of at least one other pharmaceutically acceptable salt of codeine, (ii) from about 10 mg to about 30 mg of dihydrocodeine bitartrate or an equivalent amount of at least one other pharmaceutically acceptable salt of dihydrocodeine, (iii) from about 5 mg to about 30 mg of hydrocodone bitartrate or an equivalent amount of at least one other pharmaceutically acceptable salt of hydrocodone, and the second layer may comprise one or more of an antihistamine, an expectorant and an analgesic.

In yet another aspect, the first layer may comprise from about 1 mg to about 75 mg of phenylepherine or an equivalent amount of at least one pharmaceutically acceptable salt of phenylepherine, and at least one drug which is selected from carbinoxamine, diphenhydramine, chlorpheniramine, dexbrompheniramine, carbetapentane and pharmaceutically acceptable salts thereof.

The present invention also provides a multi-layered tablet which comprises at least a first layer and a second layer. The first layer comprises phenylepherine or a pharmaceutically acceptable salt thereof and the second layer comprises at least one drug which is selected from expectorants, mucus thinning drugs, analgesics, antitussives and antihistamines.

In one aspect of the multi-layered tablet, the first layer may be an immediate release layer, or it may be a controlled-release layer. In another aspect, the second layer may be a controlled release layer.

In yet another aspect, the first layer may not contain any pharmaceutically active ingredient which is different from phenylepherine or a pharmaceutically acceptable salt thereof.

In a still further aspect, the tablet may comprise, in addition to phenylepherine or a pharmaceutically acceptable salt thereof, one or more of dextromethorphan hydrobromide, carbetapentane citrate, codeine phosphate, dihydrocodeine bitartrate, hydrocodone bitartrate, guaifenesin HBr, astemizole, azatadine maleate, bromodiphenhydramine HCl, brompheniramine maleate, carbinoxamine maleate, cetirizine HCl, chlorcyclizine HCl, chlorpheniramine maleate, clemastine fumarate, chlorothen citrate, cyclizine, cyproheptadine, desloratadine, dimethindene maleate, diphenhydramine HCl, diphenylpyraline, doxylamine, fexofenadine HCl, hydroxyine HCl, isothipendyl HCl (theruhistin), loratadine, methapyrilene fumarate, methapyrilene HCl, montelukast sodium, phenindamine tartrate, pheniramine maleate, phenyltoloxamine citrate, promethazine HCl, prophenpyridamine maleate, pyrilamine maleate, terfenadine, thenyldiamine HCl, thonzylamine, trimeprazine tartrate, tripelennamine HCl, triprolidine HCl, acetaminophen and ibuprofen.

In another aspect, the at least one drug in the second layer may have a plasma half-life which differs by at least about 1 hour from the plasma half-life of phenylepherine.

In a still further aspect, the tablet may provide a plasma concentration within the therapeutic range of the at least one drug in the second layer over a period which is coextensive with at least about 80% of the period over which the tablet provides a plasma concentration within the therapeutic range of phenylepherine.

In yet another aspect of the multi-layered tablet of the present invention, the second layer may comprise one of more of dextromethorphan, carbetapentane, codeine, dihydrocodeine, hydrocodone, guaifenesin, astemizole, azatadine, bromodiphenhydramine, brompheniramine, carbinoxamine, cetirizine, chlorcyclizine, chlorpheniramine, clemastine, chlorothen, cyclizine, cyproheptadine, desloratadine, dimethindene, diphenhydramine, diphenylpyraline, doxylamine, fexofenadine, hydroxyine, isothipendyl, loratadine, methapyrilene, methapyrilene, montelukast, phenindamine, pheniramine, phenyltoloxamine, promethazine, prophenpyridamine, pyrilamine, terfenadine, thenyldiamine, thonzylamine, trimeprazine, tripelennamine, triprolidine, acetaminophen, ibuprofen, and pharmaceutically acceptable salts thereof.

In another aspect of the multi-layer tablet, the layers thereof may be discrete zones which are arranged adjacent to each other, or one of the first and second layers may be partially or completely surrounded by the other one of the first and second layers, or one of the first and second layers may be coated with the other one of the first and second layers.

The present invention further provides a liquid dosage form which comprises (a) phenylepherine and/or a pharmaceutically acceptable salt thereof and (b) at least one drug which is selected from antitussives, expectorants, mucus thinning drugs, analgesics, and antihistamines. This dosage form provides a plasma concentration within a therapeutic range of (b) over a period which is coextensive with at least about 70% of the period over which the liquid dosage form provides a plasma concentration within the therapeutic range of (a).

In one aspect, the liquid dosage form may comprise a suspension. For example, the suspension may comprise a gel and/or the suspension may comprise particles of a complex of at least a part of component (a) and/or component (b) with an ion-exchange resin, which particles may be provided, at least in part, with a controlled release coating. The controlled release coating may comprise an organic polymer such as, e.g., a polyacrylate.

In another aspect, at least a part of (b) may be present as a complex with a complexing agent and/or at least a part of (a) may be present as a complex with a complexing agent. By way of non-limiting example, the complexing agent may comprise an ion-exchange resin such as, e.g., sodium polystyrene sulfonate.

The present invention also provides a method of concurrently alleviating a condition which can be alleviated by administering phenylepherine and at least one other condition which can be alleviated by administering at least one of an antitussive, expectorant, mucus thinning drug, analgesic or antihistamine. The method comprises administering any of the pharmaceutical dosage forms set forth above, including the various aspects thereof, to a subject in need thereof.

In one aspect of this method, the condition which can be alleviated by administering phenylepherine may comprise respiratory congestion.

In another aspect of this method, the dosage forms may be administered not more than about three times per day, e.g., not more than about twice per day.

The present invention also provides a process for making the pharmaceutical dosage form of claim 1, wherein the method comprises preparing a first composition which comprises the first drug and a second composition which comprises the at least one second drug, and combining the first and the second compositions to form the dosage form.

In one aspect of this process, the first and second compositions may be combined by using a tablet press.

The present invention also provides a pharmaceutical dosage form which comprises a first drug which comprises phenylepherine or a pharmaceutically acceptable salt thereof and has a first plasma half-life, and at least one second drug which is selected from antitussives, expectorants, mucus thinning drugs, analgesics, and antihistamines and has a second plasma half-life which differs from the first plasma half-life by at least about 2 hours. This dosage form provides a plasma concentration within a therapeutic range of the at least one second drug over a period which is coextensive with at least about 80% of the period over which the dosage form provides a plasma concentration within the therapeutic range of the first drug.

In one aspect of the dosage form, the first plasma half-life may differ by at least about 3 hours from the second plasma half-life.

In another aspect of the dosage form, the period of the plasma concentration within the therapeutic range of the at least one second drug may be coextensive with at least about 90% of the period over which the dosage form provides a plasma concentration within the therapeutic range of the first drug.

In yet another aspect, the dosage form may comprise a multi-layered tablet.

In a still further aspect, the dosage form may be associated with instructions to administer the dosage form three or fewer times per day, e.g., once or twice per day.

The present invention also provides a pharmaceutical dosage form which comprises (a) phenylepherine or a pharmaceutically acceptable salt thereof in a first form or layer and (b) phenylepherine or a pharmaceutically acceptable salt thereof in a second form or layer which is different from the first form or layer. This dosage form releases the phenylepherine (b) over a different period and at a different rate than the phenylepherine (a).

In one aspect of the dosage form, the first form or layer may an immediate release form or layer and the second form or layer may be a controlled release form or layer.

In another aspect, the dosage form may comprise a multi-layered tablet which comprises at least one immediate release layer and at least one controlled release layer which independently comprise at least phenylepherine or a pharmaceutically acceptable salt thereof and wherein at least one of the layers comprises an additional drug. The at least one additional drug may, for example, be selected from antitussives, expectorants, mucus thinning drugs, analgesics and antihistamines. Also, the immediate release layer of the multi-layered tablet may comprise the at least one additional drug, or the at least one controlled release layer thereof may comprise the at least one additional drug.

In another aspect, the dosage form may comprise a liquid which comprises phenylepherine or a pharmaceutically acceptable salt thereof in uncomplexed form and phenylepherine or a pharmaceutically acceptable salt thereof as a complex with a complexing agent. By way of non-limiting example, the complexing agent may comprise an ion-exchange resin. In another aspect, the liquid may comprise a suspension.

In another aspect, the dosage form may release phenylepherine or a pharmaceutically acceptable salt thereof independently over a first period and over a second period and not more than about 30% of the second period may be coextensive with all or a part of the first period. For example, there may be substantially no overlap between the first and second periods.

The present invention also provides a pharmaceutical dosage form which comprises at least about 37 mg of phenylepherine or an equivalent amount of a pharmaceutically acceptable salt thereof.

In one aspect, the dosage form may comprise at least about 40 mg of phenylepherine or an equivalent amount of a pharmaceutically acceptable salt thereof, for example, at least about 45 mg, or at least about 50 mg.

In another aspect, the dosage form may comprises one or more controlled release forms or layers of phenylepherine and/or a pharmaceutically acceptable salt thereof.

In another aspect, the dosage form may additionally comprise an immediate release form or layer of phenylepherine and/or a pharmaceutically acceptable salt thereof.

In yet another aspect, the dosage form may comprise at least one additional drug. For example, the at least one additional drug may comprise one or more of an expectorant, a mucus thinning drug, an antihistamine, an antitussive drug and an analgesic.

In a still further aspect, the dosage form may comprise a solid dosage form such as, e.g., a tablet, preferably, a multi-layered tablet, or the dosage form may comprise a liquid dosage form such as, e.g., a suspension.

The present invention also provides a pharmaceutical dosage form which comprises at least one controlled release form or layer of phenylepherine or a pharmaceutically acceptable salt thereof. This dosage form is associated with instructions to administer the dosage form to a subject in need thereof every x hours and the resultant amount thereby administered every x hours divided by x is at least about 5 mg of phenylepherine or an equivalent amount of a pharmaceutically acceptable salt thereof.

In one aspect, the amount thereby administered may be at least about 6 mg, e.g., at least about 7 mg; or at least about 8 mg, of phenylepherine or an equivalent amount of a pharmaceutically acceptable salt thereof.

In another aspect, the dosage form may additionally comprise an immediate release form or layer of phenylepherine and/or a pharmaceutically acceptable salt thereof.

In yet another aspect, the dosage form may comprise at least one additional drug, for example, one or more of an expectorant, a mucus thinning drug, an antihistamine, an antitussive drug and an analgesic.

In another aspect, the dosage form may comprise a solid dosage form, e.g., a tablet, for example a multi-layered tablet, or the dosage form may comprise a liquid dosage form such as, e.g., a suspension.

The present invention also provides a method of alleviating a condition which can be alleviated by administering phenylepherine. The method comprises the administration to a subject in need thereof in intervals of x hours, of a pharmaceutical dosage form which comprises phenylepherine or a pharmaceutically acceptable salt thereof. In this method, x is at least about 4 and the amount of phenylepherine or pharmaceutically acceptable salt thereof administered per interval, expressed as mg of phenylepherine free base, is at least about 5·x.

In one aspect of this method, x may be at least about 6, or at least about 8, or at least about 10.

In another aspect of this method, the amount may be at least about 6·x, or at least about 7·x, or at least about 8·x.

In a still further aspect, the condition which can be alleviated by administering phenylepherine may comprise respiratory congestion.

In yet another aspect, the dosage form may comprise at least one controlled release form or layer of the phenylepherine or pharmaceutically acceptable salt thereof.

In another aspect, the dosage form may comprise at least one additional drug, for example, one or more of an expectorant, a mucus thinning drug, an antihistamine, an antitussive drug and an analgesic.

In another aspect of the method, the dosage form may comprise a tablet, such as a multi-layered tablet, or the dosage form may comprise a liquid dosage form such as a suspension (e.g., a gel).

The present invention also provides a method of dosing phenylepherine or a pharmaceutically acceptable salt thereof which is present in a dosage form for administration in intervals of not less than about 4 hours. The method comprises administering the dosage form every x hours in a quantity which is equivalent to at least 5·x milligrams of phenylepherine free base.

The pharmaceutical dosage form which constitutes one aspect of the present invention comprises a first drug which is selected from phenylepherine or a pharmaceutically acceptable salt thereof. The preferred salt of phenylepherine is hydrochloride. However, any other pharmaceutically acceptable salt of phenylepherine may be used as well. For example, phenylepherine tannate is another example of a preferred salt for the purposes of the present invention. The term "pharmaceutically acceptable salts" as used herein refers to those salts of a particular drug that are not substantially toxic at the dosage administered to achieve the desired effect and do not independently possess significant pharmacological activity. The salts included within the scope of this term are pharmaceutically acceptable acid addition salts of a suitable inorganic or organic acid. Non-limiting examples of suitable inorganic acids are, for example hydrochloric, hydrobromic, sulfuric and phosphoric acids. Non-limiting examples of suitable organic acids include carboxylic acids, such as acetic, propionic, tannic, glycolic, lactic, pyruvic, malonic, succinic, fumaric, malic, tartaric, citric, cyclamic, ascorbic, maleic, hydroxymaleic, benzoic, phenylacetic, 4-aminobenzoic, 4-hydroxybenzoic, anthranillic, cinnamic, salicylic, 4-aminosalicyclic, 2-phenoxybenzoic, 2-acetoxybenzoic and mandelic acids, as well as sulfonic acids, such as methanesulfonic, ethanesulfonic, and β-hydroxyethanesulfonic acids.

In addition to the phenylepherine and/or pharmaceutically acceptable salt thereof, some dosage forms of the present invention will contain one or more (e.g., one, two or three) additional drugs. Preferred, non-limiting examples of such second drugs are antitussives, pain relieving agents, expectorants and mucus thinning drugs (such as, e.g., guaifenesin), and antihistamines (such as, e.g., chlorpheniramine, diphenhydramine, carbinoxamine, promethazine, and pharmaceutically acceptable salts thereof).

Preferred dosage forms of the present invention provide a plasma concentration within the therapeutic range of the at least one addditional drug over a period which is coextensive with (overlaps) at least about 70%, more preferred at least about 80%, e.g., at least about 90%, at least about 95%, or about 100%, of the period over which the dosage form provides a plasma concentration within the therapeutic range of the phenylepherine. The term "therapeutic range" as used herein and in the appended claims refers to the range of drug levels within which most patients will experience a significant therapeutic effect (including alleviation of symptoms) without an undesirable degree of adverse reactions. It is noted that the term "coextensive with" does not exclude, but rather includes, cases where a part of the period over which the plasma concentration of the at least one additional drug (and/or active metabolites thereof) is within the therapeutic range is outside the period over which the plasma concentration of the phenylepherine is within the therapeutic range. In other words, even if the corresponding period for the at least one additional drug is to overlap, for example, 70% of the corresponding period of the phenylepherine, a certain percentage (preferably not more than about 30%, e.g., not more than about 20%, not more than about 10% or even not more than about 5%) of the total period over which the plasma concentration of the at least one additional drug is within the therapeutic range may be outside the period over which the plasma concentration of the phenylepherine is within the therapeutic range.

The period over which the therapeutic range of a particular drug may be provided in a given case depends, at least in part, on the plasma half-life of the drug (including any active metabolites thereof). The term "plasma half-life" as used herein refers to the time required for the plasma drug concentration to decline by 50%. The shorter the plasma half-life of a particular drug, the shorter will be the period within the therapeutic range of the drug which is provided by a single administered dose of the drug. In one preferred aspect of the dosage form of the present invention, the plasma half-life of the at least one second drug will be shorter or longer than the plasma half-life of the phenylepherine by at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, or at least about 12 hours.

A preferred, although non-limiting, embodiment of the dosage form of the present invention is a tablet, in particular, a bi-layered tablet. Non-limiting examples of other embodiments of the dosage form of the invention are capsules, pills, chewable tablets, extended/sustained/delayed release single layer matrix tablets, suspensions, solutions, syrups, and suppositories.

The bi-layered tablet which forms another aspect of the present invention comprises two layers. The first layer comprises phenylepherine and/or a pharmaceutically acceptable salt thereof, as discussed above. The second layer may also comprise phenylepherine and/or a pharmaceutically acceptable salt thereof, for example, in a release form which is different from that in the first layer. Additionally or alternatively, the second layer comprises at least one additional drug, preferably, at least one drug which is selected from antitussives, pain relieving agents, expectorants, mucus thinning drugs, and antihistamines. Specific and non-limiting examples of such drugs are given above. In a preferred embodiment, the bi-layered tablet provides a plasma concentration within the therapeutic range of the at least one additional drug over a period which is coextensive with at least about 70%, more preferably at least about 80%, e.g., at least about 90% or even about 100% of the period over which the bi-layered tablet provides a plasma concentration within the therapeutic range of the phenylepherine.

In a particularly preferred aspect of the bi-layered tablet, the phenylepherine and/or pharmaceutically acceptable salt thereof is the only active ingredient in the first layer. The second layer will usually contain, one, two, three or even more additional drugs.

In another preferred aspect of the bi-layered tablet, the first layer is an immediate release layer and the second layer is a controlled release layer. In another preferred aspect, both layers are controlled release layers, but preferably with different release characteristics regarding release rate, start of release etc. The term "controlled release layer" as used herein and in the appended claims refers to any layer that is not an immediate release layer, i.e., does not release all of the active ingredient(s) contained therein within a relatively short time (for example, within less than 1 hour, e.g., less than 0.5 hours, following ingestion of the dosage form). Accordingly, this term is a generic term which encompasses, e.g., sustained (extended) release layers, pulsed release layers, delayed release layers, and the like. Preferably, the controlled release layer releases the one or more active ingredients contained therein continuously or intermittently and, preferably, in approximately equal amounts per time unit, over an extended period of time such as, e.g., at least about 2 hours, at least about 3 hours, at least about 4 hours, or at least about 6 hours, or at least about 8 hours or at least about 10 hours or at least about 11 hours. The desirable length of the time period of continuous or intermittent (e.g., pulsed) release depends, inter alia, on the plasma half-life of the drug and/or an active metabolite thereof.

The first layer of the bi-layered tablet of the present invention will usually contain at least about 4 mg, e.g., at least about 6.5 mg, at least about 10 mg, at least about 15 mg, at least about 20 mg, or at least about 25 mg of phenylepherine or the equivalent amount of one or more pharmaceutically acceptable salts thereof. Usually, the first layer will not contain more than about 75 mg, e.g., not more than about 60 mg, not more than about 50 mg, not more than about 45 mg, or not more than about 40 mg of phenylepherine or the equivalent amount of one or more pharmaceutically acceptable salts thereof.

The second layer of the bi-layered tablet preferably is a controlled release layer, in particular, a sustained release layer. The controlled release layer may contain, by way of non-limiting example, (i) phenylepherine hydrochloride, usually in an amount which is not less than about 1 mg, e.g., not less than about 10 mg, or not less than about 15 mg, but not more than about 75 mg, e.g., not more than about 50 mg, or equivalent amounts of any other pharmaceutically acceptable salt of phenylepherine; (ii) chlorpheniramine maleate, usually in an amount which is not less than about 0.1 mg, e.g., not less than about 2 mg, or not less than about 4 mg, but not more than about 16 mg, e.g., not more than about 12 mg, or equivalent amounts of any other pharmaceutically acceptable salts of chlorpheniramine; and/or (iii) promethazine hydrochloride, usually in an amount which is not less than about 0.1 mg. e.g., not less that about 6 mg, but not more than about 75 mg, e.g., not more than about 50 mg, and/or (iv) guaifenesin, usually in an amount which is not less than about 1 mg, e.g., not less than about 10 mg, not less than about 25 mg, or not less than about 50 mg, or not less than about 100 mg, but not more than about 2400 mg, e.g, not more than about 1200 mg, or not more than about 600 mg, and/or (vi) carbinoxamine maleate, usually in an amount which is not less than about 0.1 mg. e.g., not less that about 6 mg, but not more than about 32 mg, or equivalent amounts of any other pharmaceutically acceptable salt of carbinoxamine and/or (vii) diphenhydramine hydrochloride, usually in an amount which is not less than about 10 mg, e.g., not less that about 15 mg, or not less that about 25 mg, but not more than about 200 mg, or equivalent amounts of any other pharmaceutically acceptable salt of thereof.

Another aspect of the present invention is a multi-layered tablet which comprises at least a first layer and a second layer, but may optionally comprise a third, fourth, fifth, etc. layer. The first layer, which may be an immediate release or a controlled release layer, comprises phenylepherine, or a pharmaceutically acceptable salt thereof and the mandatory second layer usually is a controlled release layer and may comprise phenylepherine or a pharmaceutically acceptable salt thereof and/or at least one other drug, preferably selected from antitussives, pain relieving agents, expectorants, mucus thinning drugs, and antihistamines. If more than one additional drug is to be incorporated in the tablet, the second layer may contain all of the additional drugs. Alternatively, a separate (third) layer may be provided for the second additional drug, for example, in cases where it would be difficult to design a controlled release layer which provides a desired release rate for both the first and the second additional drug. Of course, a fourth, fifth, etc. layer may be provided for a third or fourth additional drug, and so on. Alternatively and by way of non-limiting example, the second and a third layer may contain the same drug or drugs, but in different (relative) concentrations and/or incorporated in a different controlled release formulation.

The multi-layered tablet of the present invention will frequently be made up of two or more distinct layers or discrete zones of granulation compressed together with the individual layers lying on top of one another. Layered tablets have the appearance of a sandwich because the edges of each layer or zone are exposed. These layered tablets are prepared by compressing a granulation onto a previously compressed granulation. The operation may be repeated to produce multi-layered tablets of more than two layers. In a preferred embodiment of the multi-layered tablet of the present invention, the tablet consists of two layers.

It is to be noted that it is not necessary for the two or more individual layers of the multi-layered tablet of the present invention to lie on top of one another. By way of non-limiting example, a second layer (e.g., sustained release layer) may be partially or completely surrounded by a first layer (e.g., an immediate release layer). For example, the second layer may be coated with the first layer. In the case of three layers, for example, the third layer may be partially or completely coated with the second layer, which in turn may be partially or completely coated with the first layer. Of course, these are but a few examples of the many different ways in which the various layers of the multi-layered tablet of the present invention can be arranged relative to each other. Moreover, it is to be understood that the tablets of the present invention are not limited to such multi-layered tablets. By way of non-limiting example, the tablet may comprise an immediate release matrix which comprises phenylepherine, or a pharmaceutically acceptable salt thereof, which matrix has dispersed therein particles of one or more sustained release formulations which have any of the other desired drug(s) incorporated therein, or vice versa.

In another aspect of the multi-layered tablet, the at least one drug in the second layer (and/or in the additional layers) may have a plasma half-life which is shorter or longer by at least about one hour, e.g., by at least about 2 hours, by at least about 3 hours, by at least about 4 hours, by at least about 5 hours, by at least about 6 hours, by at least about 7 hours, by at least about 8 hours, by at least about 9 hours, by at least about 10 hours, or by at least about 12 hours than the plasma half-life of phenylepherine, or a pharmaceutically acceptable salt thereof.

In another aspect of the multi-layered tablet, the tablet may provide a plasma concentration within a therapeutic range of the at least one drug in the second layer (e.g., an antitussive, a pain relieving agent, an expectorant, a mucus thinning drug, and/or an antihistamine) over a period which is coextensive with at least about 70%, e.g., at least about 80%, or at least about 90%, of the period over which the multi-layered tablet provides a plasma concentration within the therapeutic range of the drug(s) in the first layer, preferably phenylepherine and/or a pharmaceutically acceptable salt thereof.

Another aspect of the present invention is formed by a liquid dosage form, preferably a suspension, or a gel, which comprises (a) phenylepherine, or a pharmaceutically acceptable salt thereof and (b) at least one drug which is selected from antitussives, pain relieving agents, expectorants, mucus thinning drugs, and antihistamines. This liquid dosage form provides a plasma concentration within the therapeutic range of component (b) over a period which is coextensive with at least about 70%, preferably at least 80%, e.g., at least 90%, of the period over which the liquid dosage form provides a plasma concentration within the therapeutic range of component (a). This may be accomplished in various ways. By way of non-limiting example, component (b) may be incorporated into a solid controlled release formulation. For example, particles of component (b) may be provided with a controlled release coating (e.g. a controlled release coating comprising an organic polymer such as, e.g., a polyacrylate). This formulation may then be comminuted, if necessary, in an appropriate manner (e.g., by milling) to form particles of a size which is small enough to be suitable for being suspended in a pharmaceutically acceptable liquid carrier. Component (a), on the other hand, may be used as such or incorporated as an ion-exchange complex, or incorporated in a solid immediate release formulation, comminuted and incorporated into the liquid carrier as well. A non-limiting example of a corresponding procedure is described in the Examples provided in this application.

Prior to incorporating components (a) and (b) into a pharmaceutically acceptable liquid carrier to form a liquid dosage form, for example, a suspension, or a gel form according to the present invention, at least a part of component (a) and/or at least a part of component (b) may be transformed into a complex with a complexing agent. Non-limiting examples of suitable complexing agents comprise ion-exchange resins such as, e.g., (sodium) polystyrene sulfonate.

The dosage forms of the present invention can be manufactured by processes which are well known to those of skill in the art. For example, for the manufacture of bi-layered tablets, the active ingredients may be dispersed uniformly into a mixture of excipients, for example, by high shear granulation, low shear granulation, fluid bed granulation, or by blending for direct compression. Excipients may include diluents, binders, disintegrants, dispersants, lubricants, glidants, stabilizers, surfactants and colorants. Diluents, also termed "fillers", are typically used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders impart cohesive qualities to a tablet formulation and are used to ensure that a tablet remains intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants facilitate tablet manufacture; non-limiting examples thereof include magnesium stearate, calcium stearate, stearic acid, glyceryl behenate, and polyethylene glycol. Disintegrants facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc and the like. Stabilizers inhibit or retard drug decomposition reactions, including oxidative reactions. Surfactants may be anionic, cationic, amphoteric or nonionic. If desired, the tablets may also contain minor amounts of nontoxic auxiliary substances such as pH buffering agents, preservatives, e.g., antioxidants, wetting or emulsifying agents, solubilizing agents, coating agents, flavoring agents, and the like.

Extended/sustained release formulations may be made by choosing the right combination of excipients that slow the release of the active ingredients by coating or temporarily bonding or decreasing the solubility of the active ingredients. Examples of these excipients include cellulose ethers such as hydroxypropylmethylcellulose (e.g., Methocel K4M), polyvinylacetate-based excipients such as, e.g., Kollidon SR, and polymers and copolymers based on methacrylates and methacrylic acid such as, e.g., Eudragit NE 30D.

There are several commercially available tablet presses capable of making bi-layered tablets. For example, Manesty RotaPress Diamond, a 45 station D tooling press, is capable of making bi-layered tablets described in this application. Non-limiting examples of presses for the manufacture of bi-layered tablets include Fette America Model No. PT 3090; Maneklal Global Exports (Mumbai, India) Models JD and DH series; Niro Pharma Systems, Model R292F; and Korsch AG Models XL 800 and XL 400.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

The following Examples illustrate the use of phenylepherine or a pharmaceutically acceptable salt thereof as a respiratory decongestant.

Example 1

Bi-Layered Tablet (Wet Granulation)

A bi-layered tablet in accordance with the present invention which comprises phenylepherine hydrochloride in a first sustained release layer and guaifenesin in a second sustained release layer is illustrated as follows:

| Ingredients | Weight/tablet (mg) | Weight (kg) |
|---|---|---|
| Layer 1 (Sustained release) | | |
| Phenylepherine HCl | 60.0 | 6.0 |
| Methocel K15M | 100.0 | 10.0 |
| Silicified Microcrystalline Cellulose | 50.0 | 5.0 |
| Eudragit NE | 42.0 | 4.2 |
| Magnesium Stearate | 8.0 | 8.0 |
| Layer 2 (Sustained release) | | |
| Guaifenesin | 600.0 | 60.0 |
| Microcrystalline Cellulose (PH 102) | 45.0 | 45.0 |
| Eudragit NE | 15.0 | 15.0 |
| Methocel K4M Premium | 140.0 | 14.0 |
| Stearic Acid | 20.0 | 2.0 |
| Magnesium Stearate | 5.0 | 0.5 |
| Total | 1085.0 | 108.5 |

Procedure:

(a) Sustained release layer #1: Mix phenylepherine hydrochloride in Methocel®K15M and silicified microcrystalline cellulose in a high shear mixer/granulator for 10 minutes. Granulate the above blend using a Eudragit® NE (30%). Dry the granulation until the LOD (weight loss on drying) is less than 2.0%. Screen granules through a US sieve size #14. Add the granules and the prescreened magnesium stearate in a V shaped blender and mix for 3 minutes.

(b) Sustained release layer #2: Screen all ingredients through a US sieve size #30. Mix guaifenesin, microcrystalline cellulose PH 102, and stearic acid in a high shear mixer/granulator for 10 minutes. Granulate the above blend using a Eudragit® NE (30%). Add the Methocel®K4M to the granulator and post mix for 5 minutes. Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 260 mg and layer #2 is 825 mg. Capsules may be manufactured by filling the same proportions into capsules.

Example 2

Bi-Layered Tablet (Wet Granulation)

A bi-layered tablet in accordance with the present invention which comprises promethazine hydrochloride in an immediate release layer and phenylepherine hydrochloride in a sustained release layer is illustrated as follows:

| Ingredients | Weight/tablet (mg) | Weight batch (Kg) |
|---|---|---|
| Layer 1 (Immediate release) | | |
| Promethazine HCl | 25.0 | 25.0 |
| Silicified Microcrystalline Cellulose | 161.0 | 161.0 |
| Povidone | 3.0 | 3.0 |
| Croscarmellose Sodium | 10.0 | 10.0 |
| Magnesium Stearate | 1.0 | 1.0 |
| Layer 2 (Sustained release) | | |
| Phenylepherine hydrochloride | 30.0 | 30.0 |
| Microcrystalline Cellulose (PH 102) | 25.0 | 25.0 |
| Dicalcium Phosphate | 50.0 | 50.0 |
| Povidone | 15.0 | 15.0 |
| Methocel K4M Premium | 205.0 | 205.0 |
| Stearic Acid | 20.0 | 20.0 |
| Magnesium Stearate | 5.0 | 5.0 |
| Total | 550.0 | 550.0 |

Procedure:

(a) Immediate release layer #1: Mix the promethazine HCl, silicified microcrystalline cellulose and croscarmellose sodium, in a high shear mixer/granulator for 10 minutes. Granulate the above blend using a 30% povidone solution (3.0 g povidone in 10.0 g purified water). Dry the granulation until the LOD is less than 2.0%. Screen granules through a US sieve size #14. Add the granules and the prescreened magnesium stearate in a V shaped blender and mix for 3 minutes.

(b) Sustained release layer #2: Mix the phenylepherine hydrochloride, microcrystalline cellulose PH 102, dicalcium phosphate, Methocel K4M Premium and stearic acid in a high shear mixer/granulator for 10 minutes. Granulate the above blend using a 30% povidone solution (15.0 g povidone in 50.0 g purified water). Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 200 mg and layer #2 is 350 mg. Capsules may be manufactured by filling the same proportions into capsules.

Example 3

Bi-Layered Tablet (Wet Granulation)

A bi-layered tablet in accordance with the present invention which comprises phenylepherine hydrochloride and carbinoxamine maleate in a first sustained release layer and phenylepherine hydrochloride in a second sustained release layer is illustrated as follows:

| Ingredients | Weight/tablet (mg) | Weight batch (Kg) |
|---|---|---|
| Layer 1 (Sustained release) | | |
| Phenylepherine HCl | 75.0 | 75.0 |
| Carbinoxamine Maleate | 8.0 | 8.0 |
| Methocel K4M | 120.0 | 120.0 |
| Silicified Microcrystalline Cellulose | 30.0 | 30.0 |
| Eudragit NE | 15.0 | 15.0 |
| Magnesium Stearate | 3.0 | 3.0 |
| Layer 2 (Sustained release) | | |
| Phenylepherine hydrochloride | 30.0 | 30.0 |
| Microcrystalline Cellulose (PH 102) | 65.0 | 65.0 |
| Eudragit NE | 20.0 | 20.0 |
| Methocel K4M Premium | 113.0 | 113.0 |
| Stearic Acid | 20.0 | 20.0 |
| Magnesium Stearate | 5.0 | 5.0 |
| Total | 500.0 | 500.0 |

Procedure:

(a) Sustained release layer #1: Mix the phenylepherine HCl, carbinoxamine maleate, Methocel®K4M and silicified microcrystalline cellulose in a high shear mixer/granulator for 10 minutes. Granulate the above blend using a Eudragit® NE (30%). Dry the granulation until the LOD is less than 2.0%. Screen granules through a US sieve size #14. Add the granules and the prescreened magnesium stearate in a V shaped blender and mix for 3 minutes.

(b) Sustained release layer #2: Screen all ingredients through a US sieve size #30. Mix the phenylepherine hydrochloride, microcrystalline cellulose PH 102, and stearic acid in a high shear mixer/granulator for 10 minutes. Granulate the above blend using a Eudragit® NE (30%). Add the Methocel®K4M to the granulator and post mix for 5 minutes. Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 250 mg and layer #2 is 250 mg. Capsules may be manufactured by filling the same proportions into capsules.

Example 4

Bi-Layered Tablet (Wet Granulation)

A bi-layered tablet in accordance with the present invention which comprises phenylepherine hydrochloride and diphenhydramine hydrochloride in a first sustained release layer and codeine phosphate in a second sustained release layer is illustrated as follows:

| Ingredients | Weight/tablet (mg) | Weight batch (Kg) |
|---|---|---|
| Layer 1 (Sustained release) | | |
| Phenylepherine HCl | 120.0 | 120.0 |
| Diphenhydramine HCl | 12.0 | 12.0 |
| Methocel K4M | 200.0 | 200.0 |
| Silicified Microcrystalline Cellulose | 35.0 | 35.0 |
| Eudragit NE | 20.0 | 20.0 |
| Magnesium Stearate | 3.0 | 3.0 |
| Layer 2 (Sustained release) | | |
| Codeine Phosphate | 30.0 | 30.0 |
| Microcrystalline Cellulose (PH 102) | 55.0 | 55.0 |
| Eudragit NE | 15.0 | 31.7 |
| Methocel K4M Premium | 138.0 | 138.0 |
| Stearic Acid | 20.0 | 20.0 |
| Magnesium Stearate | 2.0 | 2.0 |
| Total | 650.0 | 650.0 |

Procedure:

(a) Sustained release layer #1: Mix the phenylepherine HCl, diphenhydramine hydrochloride, Methocel®K4M and silicified microcrystalline cellulose in a high shear mixer/granulator for 10 minutes. Granulate the above blend using a Eudragit® NE (30%). Dry the granulation until the LOD is less than 2.0%. Screen granules through a US sieve size #14. Add the granules and the prescreened magnesium stearate in a V shaped blender and mix for 3 minutes.

(b) Sustained release layer #2: Screen all ingredients through a US sieve size #30. Mix the codeine phosphate, microcrystalline cellulose PH 102, and stearic acid in a high shear mixer/granulator for 10 minutes. Granulate the above blend using a Eudragit® NE (30%). Add the Methocel®K4M to the granulator and post mix for 5 minutes. Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 390 mg and layer #2 is 260 mg. Capsules may be manufactured by filling the same proportions into capsules.

Example 5

Bi-Layered Tablet (Wet Granulation)

A bi-layered tablet in accordance with the present invention which comprises carbinoxamine maleate in a first sustained release layer and phenylepherine hydrochloride in a second sustained release layer is illustrated as follows:

| Ingredients | Weight/tablet (mg) | Weight batch (Kg) |
|---|---|---|
| Layer 1 (Sustained release) | | |
| Carbinoxamine Maleate | 8.0 | 8.0 |
| Lactose Monohydrate | 61.0 | 61.0 |
| Methocel K4M | 70.0 | 70.0 |
| Silicified Microcrystalline Cellulose | 39.0 | 39.0 |
| Eudragit NE | 20.0 | 20.0 |
| Magnesium Stearate | 2.0 | 2.0 |
| Layer 2 (Sustained release) | | |
| Phenylepherine hydrochloride. | 30.0 | 30.0 |
| Microcrystalline Cellulose (PH 102) | 45.0 | 45.0 |
| Eudragit NE | 15.0 | 15.0 |
| Methocel K4M Premium | 103.0 | 103.0 |
| Stearic Acid | 20.0 | 20.0 |
| Magnesium Stearate | 2.0 | 2.0 |
| Total | 415.0 | 415.0 |

Procedure:

(a) Sustained release layer #1: Mix the carbinoxamine maleate, Methocel®K4M, lactose monohydrate and silicified microcrystalline cellulose in a high shear mixer/granulator for 10 minutes. Granulate the above blend using a Eudragit® NE (30%). Dry the granulation until the LOD is less than 2.0%. Screen granules through a US sieve size #14. Add the granules and the prescreened magnesium stearate in a V shaped blender and mix for 3 minutes.

(b) Sustained release layer #2: Screen all ingredients through a US sieve size #30. Mix the phenylepherine hydrochloride, microcrystalline cellulose PH 102, and stearic acid in a high shear mixer/granulator for 10 minutes. Granulate the above blend using a Eudragit® NE (30%). Add the Methocel®K4M to the granulator and post mix for 5 minutes. Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 200 mg and layer #2 is 215 mg. Capsules may be manufactured by filling the same proportions into capsules.

Example 6

Bi-Layered Tablet (Direct Compression)

A bi-layered tablet in accordance with the present invention which comprises promethazine hydrochloride (longer half-life drug) in an immediate release layer and phenylepherine hydrochloride (shorter half-life drug) in a sustained release layer is illustrated as follows:

| Ingredients | Weight/tablet (mg) | Weight batch (Kg) |
|---|---|---|
| Layer 1 (Immediate release) | | |
| Promethazine HCl | 25.0 | 25.0 |
| Silicified Microcrystalline Cellulose | 114.0 | 114.0 |
| Sodium Starch Glycolate | 10.0 | 10.0 |
| Magnesium Stearate | 1.0 | 1.0 |
| Layer 2 (Sustained release) | | |
| Phenylepherine hydrochloride | 60.0 | 60.0 |
| Lactose Monohydrate | 50.0 | 50.0 |
| Dicalcium Phosphate | 50.0 | 50.0 |
| Kollidon SR | 220.0 | 220.4 |
| Stearic acid | 15.0 | 15.0 |
| Magnesium Stearate | 5.0 | 5.0 |
| Total | 550.0 | 550.0 |

Procedure:

(a) Immediate release layer #1: Screen all ingredients through a US sieve size #30. Blend the promethazine hydrochloride, microcrystalline cellulose and sodium starch glycolate for 20 minutes. Add magnesium stearate to the above blend and mix for an additional time of three minutes.

(b) Sustained release layer #2: Blend the phenylepherine hydrochloride, lactose monohydrate, dicalcium phosphate and Kollidon® SR for 20 minutes. Add stearic acid and magnesium stearate to the above blend and mix for an additional time of three minutes.

Manufacture bi-layered tablets using a rotary bi-layer tablet press where in each tablet the immediate release layer #1 is 150 mg and the sustained release layer #2 is 400 mg. Capsules may be manufactured by filling the same proportions into capsules.

Example 7

Bi-Layered Tablet (Wet Granulation)

A bi-layered tablet in accordance with the present invention which comprises phenylepherine tannate and chlorpheniramine tannate in an immediate release layer and phenylepherine tannate in a sustained release layer is illustrated as follows:

| Ingredients | Weight/tablet (mg) | Weight batch (Kg) |
|---|---|---|
| Layer 1 (Immediate release) | | |
| Phenylepherine Tannate | 60.0 | 60.0 |
| Chlorpheniramine Tannate | 8.0 | 8.0 |
| Silicified Microcrystalline Cellulose | 208.0 | 208.0 |
| Povidone | 3.0 | 3.0 |
| Croscarmellose Sodium | 10.0 | 10.0 |
| Magnesium Stearate | 1.0 | 1.0 |
| Layer 2 (Sustained release) | | |
| Phenylepherine tannate | 30.0 | 30.0 |
| Microcrystalline Cellulose (PH 102) | 30.0 | 30.0 |
| Dicalcium Phosphate | 100.0 | 100.0 |
| Povidone | 15.0 | 15.0 |
| Methocel K4M Premium | 210.0 | 210.0 |
| Stearic Acid | 20.0 | 20.0 |
| Magnesium Stearate | 5.0 | 5.0 |
| Total | 700.0 | 700.0 |

Procedure:

(a) Immediate release layer #1: Mix the phenylepherine tannate, chlorpheniramine tannate, silicified microcrystalline cellulose and croscarmellose sodium, in a high shear mixer/granulator for 10 minutes. Granulate the above blend using a 30% povidone solution (3.0 Kg povidone in 7.0 Kg purified water). Dry the granulation until the LOD is less than 2.0%. Screen granules through a US sieve size #14. Add the granules and the prescreened magnesium stearate in a V shaped blender and mix for 3 minutes.

(b) Sustained release-layer #2: Mix the Phenylepherine tannate, microcrystalline cellulose PH 102, dicalcium phosphate, Methocel K4M Premium and stearic acid in a high shear mixer/granulator for 10 minutes. Granulate the above blend using a 30% povidone solution (15.0 Kg povidone in 35.0 Kg purified water). Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 290 mg and layer #2 is 410 mg. Capsules may be manufactured by filling the same proportions into capsules.

Example 8

Bi-Layered Tablet (Wet Granulation)

A bi-layered tablet in accordance with the present invention which comprises diphenhydramine hydrochloride in an immediate release layer and phenylepherine hydrochloride in a sustained release layer is illustrated as follows:

| Ingredients | Weight/tablet (mg) | Weight batch (Kg) |
|---|---|---|
| Layer 1 (Immediate release) | | |
| Diphenhydramine HCl | 100.0 | 100.0 |
| Silicified Microcrystalline Cellulose | 86.0 | 86.0 |
| Povidone | 3.0 | 3.0 |
| Croscarmellose Sodium | 10.0 | 10.0 |
| Magnesium Stearate | 1.0 | 1.0 |
| Layer 2 (Sustained release) | | |
| Phenylepherine HCl | 75.0 | 75.0 |
| Microcrystalline Cellulose (PH 102) | 30.0 | 30.0 |
| Dicalcium Phosphate | 30.0 | 30.0 |
| Povidone | 15.0 | 15.0 |
| Methocel K4M Premium | 178.0 | 178.0 |
| Stearic Acid | 20.0 | 20.0 |
| Magnesium Stearate | 2.0 | 2.0 |
| Total | 550.0 | 550.0 |

Procedure:

(a) Immediate release layer #1: Mix the diphenydramine hydrochloride, silicified microcrystalline cellulose and croscarmellose sodium, in a high shear mixer/granulator for 10 minutes. Granulate the above blend using a 30% povidone solution (3.0 g povidone in 10.0 g purified water). Dry the granulation until the LOD is less than 2.0%. Screen granules through a US sieve size #14. Add the granules and the prescreened magnesium stearate in a V shaped blender and mix for 3 minutes.

(b) Sustained release layer #2: Mix the phenylepherine hydrochloride, microcrystalline cellulose PH 102, dicalcium phosphate, Methocel K4M Premium and stearic acid in a high shear mixer/granulator for 10 minutes. Granulate the above blend using a 30% povidone solution (15.0 g povidone in 50.0 g purified water). Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 200 mg and layer #2 is 350 mg. Capsules may be manufactured by filling the same proportions into capsules.

Example 9

Bi-Layered Tablet (Direct Compression)

A bi-layered tablet in accordance with the present invention which comprises guaifenesin in a first sustained release layer and phenylepherine hydrochloride in a second sustained release layer is illustrated as follows:

| Ingredients | Weight/tablet (mg) | Weight batch (Kg) |
|---|---|---|
| Layer 1 (Sustained release) | | |
| Guaifenesin | 600.0 | 300.0 |
| Methocel K15M | 200.0 | 100.0 |
| Silicified Microcrystalline Cellulose | 72.0 | 36.0 |
| Magnesium Stearate | 8.0 | 4.0 |
| Layer 2 (Sustained release) | | |
| Phenylepherine hydrochloride | 60.0 | 30.0 |
| Dicalcium Phosphate | 70.0 | 35.0 |
| Kollidon SR | 172.0 | 86.0 |
| Stearic acid | 15.0 | 7.5 |
| Magnesium Stearate | 3.0 | 1.5 |
| Total | 1200.0 | 600.0 |

Procedure:

(a) Sustained release layer #1: Screen all ingredients through a US sieve size #30. Blend the guaifenesin, Methocel® K15M and silicified microcrystalline cellulose for 25 minutes. Add magnesium stearate to the above blend and mix for an additional time of three minutes.

(b) Sustained release layer #2: Blend the phenylepherine hydrochloride, dicalcium phosphate and Kollidon® SR for 20 minutes. Add stearic acid and magnesium stearate to the above blend and mix for an additional time of three minutes.

Manufacture bi-layered tablets using a rotary bi-layer tablet press where in each tablet layer #1 is 880 mg and layer #2 is 320 mg. Capsules may be manufactured by filling the same proportions into capsules.

Example 10

Bi-Layered Tablet (Wet Granulation)

A bi-layered tablet in accordance with the present invention which comprises brompheniramine maleate in a first sustained release layer and phenylepherine hydrochloride in a second sustained release layer is illustrated as follows:

| Ingredients | Weight/tablet (mg) | Weight batch (Kg) |
|---|---|---|
| Layer 1 (Sustained release) | | |
| Brompheniramine Maleate | 6.0 | 6.0 |
| Methocel K15M | 94.0 | 94.0 |
| Silicified Microcrystalline Cellulose | 50.0 | 50.0 |
| Eudragit NE | 42.0 | 42.0 |
| Magnesium Stearate | 8.0 | 8.0 |
| Layer 2 (Sustained release) | | |
| Phenylepherine HCl | 60.0 | 60.0 |
| Microcrystalline Cellulose (PH 102) | 45.0 | 45.0 |
| Eudragit NE | 15.0 | 15.0 |
| Methocel K4M Premium | 108.0 | 108.0 |
| Stearic Acid | 20.0 | 20.0 |
| Magnesium Stearate | 2.0 | 2.0 |
| Total | 450.0 | 450.0 |

Procedure:

(a) Sustained release layer #1: Mix the brompheniramine maleate, Methocel®K15M and silicified microcrystalline cellulose in a high shear mixer/granulator for 10 minutes. Granulate the above blend using a Eudragit® NE (30%). Dry the granulation until the LOD is less than 2.0%. Screen granules through a US sieve size #14. Add the granules and the prescreened magnesium stearate in a V shaped blender and mix for 3 minutes.

(b) Sustained release layer #2: Screen all ingredients through a US sieve size #30. Mix the phenylepherine hydrochloride, microcrystalline cellulose PH 102, dicalcium phosphate and stearic acid in a high shear mixer/granulator for 10 minutes. Granulate the above blend using a Eudragit® NE (30%). Add the Methocel®K4M to the granulator and post mix for 5 minutes. Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 200 mg and layer #2 is 250 mg. Capsules may be manufactured by filling the same proportions into capsules.

Example 11

Bi-Layered Tablet (Wet Granulation)

A bi-layered tablet in accordance with the present invention which comprises guaifenesin in a first sustained release layer and phenylepherine hydrochloride in a second sustained release layer is illustrated as follows:

| Ingredients | Weight/tablet (mg) | Weight batch (Kg) |
|---|---|---|
| Layer 1 (Sustained release) | | |
| Guaifenesin | 1000.0 | 400.0 |
| Methocel K15M | 200.0 | 80.0 |
| Silicified Microcrystalline Cellulose | 40.0 | 16.0 |
| Eudragit NE | 50.0 | 20.0 |
| Magnesium Stearate | 10.0 | 4.0 |

-continued

| Ingredients | Weight/tablet (mg) | Weight batch (Kg) |
|---|---|---|
| Layer 2 (Sustained release) | | |
| Phenylepherine hydrochloride | 30.0 | 12.0 |
| Microcrystalline Cellulose (PH 102) | 45.0 | 18.0 |
| Eudragit NE | 15.0 | 6.0 |
| Methocel K4M Premium | 100.0 | 40.0 |
| Stearic Acid | 20.0 | 8.0 |
| Magnesium Stearate | 2.0 | 0.5 |
| Total | 1510.0 | 604.0 |

Procedure:

(a) Sustained release layer #1: Mix the guaifenesin, Methocel®K15M and silicified microcrystalline cellulose in a high shear mixer/granulator for 10 minutes. Granulate the above blend using a Eudragit® NE (30%). Dry the granulation until the LOD is less than 2.0%. Screen granules through a US sieve size #14. Add the granules and the prescreened magnesium stearate in a V shaped blender and mix for 3 minutes.

(b) Sustained release layer #2: Screen all ingredients through a US sieve size #30. Mix the phenylepherine HCl, microcrystalline cellulose PH 102 and stearic acid in a high shear mixer/granulator for 10 minutes. Granulate the above blend using a Eudragit® NE (30%). Add the Methocel®K4M to the granulator and post mix for 5 minutes. Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 1300 mg and layer #2 is 210 mg. Capsules may be manufactured by filling the same proportions into capsules.

Example 12

Bi-Layered Tablet (Direct Compression)

A bi-layered tablet in accordance with the present invention which comprises phenylepherine hydrochloride in a first immediate release layer and phenylepherine hydrochloride and diphenhydramine hydrochloride in a second sustained release layer is illustrated as follows:

| Ingredients | Weight/tablet (mg) | Weight batch (Kg) |
|---|---|---|
| Layer 1 (Immediate release) | | |
| Phenylepherine hydrochloride | 30.0 | 30.0 |
| Silicified Microcrystalline Cellulose | 160.0 | 160.0 |
| Sodium Starch Glycolate | 9.0 | 9.0 |
| Magnesium Stearate | 1.0 | 1.0 |
| Layer 2 (Sustained release) | | |
| Phenylepherine HCl | 60.0 | 60.0 |
| Diphenhydramine HCl | 60.0 | 60.0 |
| Dicalcium Phosphate | 100.0 | 100.0 |
| Kollidon SR | 220.0 | 220.0 |
| Stearic acid | 16.0 | 16.0 |
| Magnesium Stearate | 4.0 | 4.0 |
| Total | 660.0 | 660.0 |

Procedure:

(a) Immediate release Layer #1: Screen all ingredients through a US sieve size #30. Preblend a portion (about a third of the total) of the silicified microcrystalline cellulose and all the phenylepherine hydrochloride for the immediate release layer for 15 minutes. Add sodium starch glycolate and mix for additional 10 minutes. Add magnesium stearate to the above blend and mix for three minutes.

(b) Sustained release layer #2: Screen all ingredients through a US sieve size #30. Preblend a portion of the Kollidon SR (about a third of the total) and all the diphenhydramine hydrochloride for 15 minutes. Add the remaining Kollidon SR, phenylepherine hydrochloride and dicalcium phosphate to the above preblend and mix for additional 20 minutes. Add stearic acid and magnesium stearate to the above blend and mix for three minutes.

Manufacture bi-layered tablets using a rotary bi-layer tablet press where in each tablet the immediate release layer is 200 mg and the sustained release layer is 460 mg.

Example 13

Bi-Layered Tablet (Direct Compression)

By using the process described in Example 12, a bi-layered tablet which contains phenylepherine hydrochloride in an immediate release layer and phenylepherine hydrochloride and dexbrompheniramine maleate in a sustained release layer (see the formula below) may be manufactured by using direct compression:

| Ingredients | Weight/tablet (mg) |
|---|---|
| Layer 1 (Immediate Release) | |
| Phenylepherine hydrochloride | 10.0 |
| Silicified Microcrystalline Cellulose | 133.5 |
| Sodium Starch Glycolate | 15.0 |
| Magnesium Stearate | 1.5 |
| Layer 2 (Sustained Release) | |
| Phenylepherine hydrochloride | 40.0 |
| Dexbrompheniramine maleate | 6.0 |
| Dicalcium Phosphate | 100.0 |
| Kollidon SR | 244.0 |
| Stearic Acid | 7.0 |
| Magnesium Stearate | 3.0 |
| Total | 560.0 |

Example 14

Bi-Layered Tablet (Wet Granulation)

A bi-layered tablet in accordance with the present invention which comprises phenylepherine hydrochloride in an immediate release layer and phenylepherine hydrochloride and chlorpheniramine maleate in a sustained release layer is illustrated as follows:

| Ingredients | Weight/tablet (mg) | Weight batch (Kg) |
|---|---|---|
| Layer 1 (Immediate release) | | |
| Phenylepherine hydrochloride | 10.0 | 10.0 |
| Silicified Microcrystalline Cellulose | 111.0 | 111.0 |
| Povidone | 3.0 | 3.0 |

-continued

| Ingredients | Weight/tablet (mg) | Weight batch (Kg) |
|---|---|---|
| Croscarmellose Sodium | 10.0 | 10.0 |
| Magnesium Stearate | 1.0 | 1.0 |
| Layer 2 (Sustained release) | | |
| Phenylepherine HCl | 60.0 | 60.0 |
| Chlorpheniramine Maleate | 8.0 | 8.0 |
| Microcrystalline Cellulose (PH 102) | 30.0 | 30.0 |
| Dicalcium Phosphate | 100.0 | 100.0 |
| Povidone | 15.0 | 15.0 |
| Methocel K4M Premium | 212.0 | 212.0 |
| Stearic Acid | 20.0 | 20.0 |
| Magnesium Stearate | 5.0 | 5.0 |
| Total | 585.0 | 585.0 |

Procedure:

(a) Immediate release layer #1: Screen all ingredients through a US sieve size #30. Blend the phenylepherine hydrochloride, silicified microcrystalline cellulose, and croscarmellose sodium in a high shear mixer/granulator for 10 minutes. Granulate the above blend using a 30% povidone solution (4.3 Kg povidone in 10.0 Kg purified water). Dry the granulation until the LOD is less than 2.0%. Screen granules through a US sieve size #14. Add granules and the prescreened magnesium stearate to the above blend and mix for 3 minutes.

(b) Sustained release layer #2: Screen all ingredients through a US sieve size #30. Blend the phenylepherine hydrochloride, chlorpheniramine maleate, microcrystalline cellulose PH 102, dicalcium phosphate and Methocel K4M Premium and stearic acid in a high shear mixer/granulator for 10 minutes. Granulate the above blend using a 30% povidone solution (15.0 Kg povidone in 35.0 Kg purified water). Dry the granulation until the LOD is less than 2.0%. Screen granules through a US sieve size #14. Add granules and the prescreened magnesium stearate to the above blend and mix for 3 minutes.

Manufacture bi-layered tablets using a rotary bi-layer tablet press where in each tablet the immediate release layer is 135 mg and the sustained release layer is 450 mg.

Example 15

Bi-Layered Tablet (Wet Granulation)

By using the process described in Example 14, a bi-layered tablet containing phenylepherine hydrochloride in an immediate release layer and phenylepherine hydrochloride and chlorpheniramine maleate in a sustained release layer may be manufactured by using wet granulation:

| Ingredients | Weight/tablet (mg) |
|---|---|
| Layer 1 (Immediate Release) | |
| Phenylepherine hydrochloride | 30.0 |
| Silicified Microcrystalline cellulose | 129.5 |
| Povidone | 4.0 |
| Croscarmellose sodium | 15.0 |
| Magnesium Stearate | 1.5 |
| Layer 2 (Sustained Release) | |
| Phenylepherine HCl | 60.0 |
| Chlorpheniramine Maleate | 8.0 |
| Microcrystalline Cellulose 102 | 30.0 |
| Lactose Monohydrate | 100.0 |
| Dicalcium Phosphate | 100.0 |
| Povidone | 15.0 |
| Hydroxypropylmethylcellulose | 212.0 |
| Stearic Acid | 20.0 |
| Magnesium Stearate | 5.0 |
| Total | 730.0 |

Example 16

Bi-Layered Tablet (Wet Granulation)

A bi-layered tablet in accordance with the present invention which comprises phenylepherine hydrochloride in a sustained release layer and carbetapentane citrate in a immediate release layer is illustrated as follows:

| | Formula | | |
|---|---|---|---|
| | | | Amounts |
| Process Steps | Ingredients | Dose (mg) | Scale-Up |
| Sustained Release Layer | | | |
| Wet Mix | RMI - PURIFIED WATER | 48.000 | 15.000 kg |
| Wet Mix | RMI - POVIDONE K-30 USP | 12.000 | 3.750 kg |
| Pre-blend | RMI - PHENYLEPHRINE HCl USP UNMIC | 40.000 | 12.500 kg |
| Pre-blend | RMI - CAL PHOSPHATE DIBASIC DIHYD | 25.000 | 7.813 kg |
| Pre-blend | RMI - PROSOLV SMCC 90 | 125.000 | 39.063 kg |
| Pre-blend | RMI - METHOCEL K4M PREMIUM USP | 50.000 | 15.625 kg |
| Final blend | RMI - METHOCEL K4M PREMIUM USP | 144.000 | 45.000 kg |
| Lube blend | RMI - MAGNESIUM STEARATE NF | 4.000 | 1.250 kg |
| Layer Weight: | | 400.000 | |
| Immediate Release Layer | | | |
| Wet Mix | RMI - PURIFIED WATER | 24.000 | 7.500 kg |
| Wet Mix | RMI - POVIDONE K-30 USP | 6.000 | 1.875 kg |
| Pre-blend | RMA - CARBETAPENTANE CITRATE | 40.000 | 12.500 kg |
| Pre-blend | RMI - PROSOLV SMCC 90 | 100.000 | 31.250 kg |
| Pre-blend | RMI - LACTOSE MONOHYDRATE #316 | 40.000 | 12.500 kg |
| Pre-blend | RMI - SODIUM STARCH GLYCOLATE | 8.000 | 2.500 kg |

-continued

Formula

| Process Steps | Ingredients | Dose (mg) | Scale-Up |
|---|---|---|---|
| Pre-blend | DYE - FD&C BLUE #1 ALUMINUM LAKE | 0.156 | 0.048 kg |
| Final blend | RMI - PROSOLV SMCC 90 | 145.688 | 45.528 kg |
| Final blend | RMI - LACTOSE MONOHYDRATE #316 | 40.000 | 12.500 kg |
| Final blend | RMI - SODIUM STARCH GLYCOLATE | 16.000 | 5.000 kg |
| Final blend | DYE - FD&C BLUE #1 ALUMINUM LAKE | 0.156 | 0.048 kg |
| Lube blend | RMI - MAGNESIUM STEARATE NF | 4.000 | 1.250 kg |
| Layer Weight: | | 400.000 | |
| Totals(wt) | | 800.000 | 250.000 kg |
| Totals (tablets) | | 1 | 312,500 |

Procedure

Sustained Release Layer (Layer 1)
1. Set aside 0.5 kg of Purified Water to be used in step 4.
2. Prepare a solution using the scale up amounts of Povidone K-30, and the remaining Purified Water from step 1.
3. Blend the pre-blend scale up amounts of Phenylephrine HCl USP, Calcium Phosphate Dibasic Dihydrate, and Prosolv SMCC 90 with a high shear mixer/granulator for 10 minutes.
4. With the mixer/granulator on, pump the solution prepared in step 2 in to the mixer/granulator. After completion, stop the mixer/granulator and rinse the container with the Purified water set aside in step 1. Pump the rinse water to the mixer/granulator with mixer on. Turn off mixer when completed.
5. Charge the pre-blend scale up amount of Methocel K4M premium to the mixer/granulator and mix for 1 minute.
6. Dry the granulation until the LOD is 4% or less.
7. Pass the dried granulation through a Fitzpatrick Fitzmill fitted with a 14 mesh screen.
8. Screen the final blend scale up amount of Methocel K4M premium through a 14 mesh screen.
9. Blend the milled granulation from step 7 and the screened materials from step 8 using a V-blender for 20 minutes.
10. Screen the lube scale up amount of Magnesium Stearate using a 30 mesh screen.
11. Transfer the screened Magnesium Stearate to the V-blender and blend for 3 minutes. When completed discharge into drums double lined with polyethylene bags.

Immediate Release Layer (Layer 2)
1. Set aside 0.5 kg of Purified Water to be used in step 4.
2. Prepare a solution using the scale up amounts Povidone K-30, and the remaining Purified Water from step 1.
3. Blend the pre-blend scale up amounts of Carbetapentane Citrate, Prosolv SMCC 90, Lactose Monohydrate #316, Sodium Starch Glycolate, and FD&C Blue #1 Aluminum Lake using a high shear mixer/granulator for 10 minutes.
4. With the mixer/granulator on, pump the solution prepared in step 2 in to the mixer/granulator. After completion, stop the mixer/granulator and rinse the container with the Purified Water set aside in step 1. Pump the rinse water to the mixer/granulator with mixer on. Allow mixture to mix for an additional minute then turn mixer/granulator off.
5. Dry the granulation until the LOD is 4% or less.
6. Pass the dried granulation through a Fitzpatrick Fitzmill fitted with a 14 mesh screen.
7. Screen the final blend scale up amounts of Prosolv SMCC 90, Lactose Monohydrate #316, Sodium Starch Glycolate, and FD&C Blue #1 Aluminum Lake through a 14 mesh screen.
8. Blend the milled granulation from step 6 and the screened materials from step 7 using a V-blender for 20 minutes.
9. Screen the lube scale up amount of Magnesium Stearate using a 30 mesh screen.
10. Transfer the screened Magnesium Stearate to the V-blender and blend for 3 minutes. When completed discharge into proper drums double lined with polyethylene bags.

Compress bi-layered tablets using a rotary bi-layer tablet press where in each tablet layer 1 is 400.0 mg and layer 2 is 400 mg.

The above examples illustrate how to manufacture a bi-layered tablet containing phenylepherine hydrochloride in (at least) a first layer and an antihistamine and/or a decongestant and/or an expectorant in (at least) a second layer. Non-limiting examples of other possible active ingredients in an exemplary range as described in the following Table 1 can be employed depending on the specific therapeutic effect desired.

TABLE 1

| Active ingredient | Amount per Tablet | Preferred Amount per Tablet | OTC Daily Dosage |
|---|---|---|---|
| ANTIHISTAMINES | | | |
| Azelastine hydrochloride | 0.1-2.0 mg | 0.125 mg | |
| Azatadine hydrochloride | 0.1-4.0 mg | 1 mg | |
| Brompheniramine maleate | 0.1-64 mg | 2-16 mg | 24 mg |
| Dexbrompheniramine maleate | 0.1-24 mg | 3-6 mg | 12 mg |
| Carbinoxamine maleate | 0.1-16 mg | 4 mg | |
| Cetirizine hydrochloride | 0.1-40 mg | 5-10 mg | |
| Chlorcyclizine | 0.1-300 mg | 50-75 | 75 mg |
| Chlorpheniramine maleate | 0.1-64 mg | 2-16 mg | 24 mg |
| Chlorpheniramine polistirex | 0.1-32 mg | 4-8 mg | |
| Clemastine | 0.1-12 mg | 0.5-2.68 mg | |
| Cyproheptadine | 0.1-16 mg | 2-4 mg | |
| Dexchlorpheniramine maleate | 0.1-24 mg | 2 mg | 12 mg |
| Cyproheptadine hydrochloride | 0.1-32 mg | 2-4 mg | |
| Diphenhydramine hydrochloride | 0.1-300 mg | 10-50 mg | 300 mg |

TABLE 1-continued

| Active ingredient | Amount per Tablet | Preferred Amount per Tablet | OTC Daily Dosage |
|---|---|---|---|
| Diphenhydramine citrate | 0.1-2000 mg | 50-450 mg | 456 mg |
| Bromodiphenhydramine hydrochloride | 0.1-200 mg | 12.5-25 mg | |
| Doxylamine succinate | 0.1-200 mg | 12.5-25 mg | 75 mg |
| Fexofenadine hydrochloride | 0.1-720 mg | 30-180 mg | |
| Hydroxyzine hydrochloride | 0.1-400 mg | 10-100 mg | |
| Hydroxyzine pamoate | 0.1-400 mg | 25-100 mg | |
| Loratadine | 0.1-80 mg | 1-10 mg | |
| Desloratadine | 0.1-40 mg | 5 mg | |
| Phenindamine tartrate | 0.1-750 mg | 10-150 mg | 150 mg |
| Pheniramine maleate | 0.1-750 mg | 10-150 mg | 150 mg |
| Pyrilamine maleate | 0.1-200 mg | 25-200 mg | 200 mg |
| Terfenadine | 0.1-100 mg | 10-100 mg | |
| Thenyldiamine | 0.1-100 mg | 10-100 mg | |
| Thonzylamine | 0.1-3000 mg | 10-600 mg | 600 mg |
| Thymol | 0.1-100 mg | 10-100 mg | |
| Tripelennamine hydrochloride | 0.1-400 mg | 25-50 mg | |
| Triprolidine hydrochloride EXPECTORANT | 0.1-40 mg | 1.25-5 mg | 10 mg |
| Guaifenesin | 0.1-2000 mg | 50-1200 | 2400 mg |

Example 17

Bi-Layered Tablet (Wet Granulation)

A bi-layered tablet in accordance with the present invention which contains phenylepherine hydrochloride in both an immediate release layer and a sustained release layer and carbetapentane citrate in both an immediate release layer and a sustained release layer is illustrated as follows:

| Ingredients | Weight/tablet (mg) | Weight batch (Kg) |
|---|---|---|
| Layer 1 (Immediate release) | | |
| Carbetapentane citrate | 15.0 | 22.5 |
| Phenylepherine hydrochloride | 15.0 | 22.5 |
| Silicified Microcrystalline Cellulose | 74.2 | 111.3 |
| Croscarmellose Sodium | 10.0 | 15.0 |
| Magnesium Stearate | 0.8 | 1.2 |
| Layer 2 (Sustained release) | | |
| Carbetapentane citrate | 45.0 | 67.5 |
| Phenylepherine hydrochloride | 45.0 | 67.5 |
| Microcrystalline Cellulose (PH 102) | 20.0 | 30.0 |
| Povidone | 8.0 | 12.0 |
| Methocel K4M Premium | 150.0 | 225.0 |
| Magnesium Stearate | 2.0 | 3.0 |
| Total | 385.0 | 577.5 |

Procedure:

(a) Immediate release layer #1: Mix the prescreened (#30 mesh) phenylepherine hydrochloride, carbetapentane citrate, silicified microcrystalline cellulose and croscarmellose sodium, in a V shaped blender for 20 minutes. Add prescreened (#40 mesh) magnesium stearate in a V shaped blender and mix for 3 minutes.

(b) Sustained release layer #2: Mix the phenylepherine hydrochloride, carbetapentane citrate, Methocel K4M Premium and microcrystalline cellulose in a high shear mixer/granulator for 10 minutes. Granulate the above blend using a 30% povidone solution (12.0 Kg povidone in 28.0 Kg purified water). Dry the granulation until the LOD is less than 2.0%. Screen granules through a US sieve size #14. Add the granules and the prescreened magnesium stearate in a V shaped blender and mix for 3 minutes.

Manufacture bi-layered tablets using a rotary bi-layer tablet press where in each tablet layer #1 is 115 mg and layer #2 is 270 mg.

Example 18

Bi-Layered Tablet (Wet Granulation)

A bi-layered tablet in accordance with the present invention which comprises phenylepherine hydrochloride and guaifenesin in two different sustained release layers is illustrated as follows:

| | | Formula | | |
|---|---|---|---|---|
| | | | Amounts | |
| Process Steps | Ingredients | | Dose(mg) | Scale-Up |
| Wet Mix | RMI - PURIFIED WATER | | 55.000 | 17.188 kg |
| Wet Mix | RMI - POVIDONE K-30 USP | | 15.000 | 4.688 kg |
| Pre-blend | RMA - GUAIFENESIN USP | | 600.000 | 187.500 kg |
| Pre-blend | RMA - PHENYLEPHRINE HCL USP | | 40.000 | 12.500 kg |
| Pre-blend | RMI - CAL PHOSPHATE DIBASIC ANHYD | | 40.000 | 12.500 kg |
| Pre-blend | RMI - METHOCEL K4M PREMIUM USP | | 16.000 | 5.000 kg |
| Final blend | RMI - STEARIC ACID NF | | 4.500 | 1.406 kg |
| Final blend | RMI - METHOCEL K4M PREMIUM USP | | 79.700 | 24.906 kg |
| Lube blend | RMI - MAGNESIUM STEARATE NF | | 4.500 | 1.406 kg |
| Color blend | DYE - FD&C BLUE #1 ALM LAKE | | 0.300 | 0.094 kg |
| Total (wt) | | | 800.000 | 250.000 kg |
| Total (tablets) | | | 1 | 312,500 |

Procedure

1. Set aside 0.5 kg of purified water to be used as a rinse in step 4.
2. Prepare a solution using the scale up amounts of Povidone K-30, and the remaining Purified Water.
3. Blend the pre-blend scale up amounts of Guaifenesin USP, Phenylephrine HCl USP, and Calcium Phosphate Dibasic Anhydrous using a high sheer mixer/granulator for 10 minutes.
4. With the mixer/granulator on, pump the solution prepared in step 2 in to the mixer/granulator. After completion, stop the mixer/granulator and rinse the container with the 0.5 kg of Purified water set aside in step 1. Pump the rinse water to the mixer/granulator with mixer on. Turn off mixer when completed.
5. Charge the pre-blend scale up amount of Methocel K4M premium to the mixer/granulator and mix for 1 minute.
6. Dry the granulation until the LOD is 1% or less.
7. Pass the dried granulation through a Fitzpatrick Fitzmill fitted with a 109 screen.
8. Screen the final blend raw materials through a 12 mesh screen.
9. Blend the milled granulation from step 7 and the screened materials from step 8 using a V-blender for 20 minutes.
10. Screen the lube blend material through a 30 mesh screen.
11. Charge the screened material from step 10 to the V-blender and blend for 2 minutes.
12. Discharge half of the blended product into proper drums double lined with polyethylene bags and set aside for step 16.
13. Screen the color blend material through a 30 mesh screen.
14. Charge the screened color blend material to the V-blender and blend for 1 minute.
15. Discharge into proper drums double lined with polyethylene bags and set aside for step 16.
16. Compress bi-layered tablets using a rotary bi-layer tablet press where in each tablet layer 1 is 400.0 mg's and layer 2 is 400.0 mg's.

Example 19

Capsule formulation

A capsule formulation in accordance with the present invention which contains phenylepherine both in an immediate release form and in a sustained release form is illustrated as follows:

| Ingredients | Amount (mg)/tablet |
| --- | --- |
| Phenylepherine Ion excange complex | Equivalent to 45 mg of Phenylepherine hydrochloride |
| Phenylepherine | 15.0 |
| Eudragit ® L 100 | 10.0 to 100.0 |
| Microcrystalline Cellulose | q.s* |
| Magnesium Stearate | 5.0 |
| Total | 500.0 |

*Added to make remainder of weight.

The formula described above serves as a non-limiting example. Any active drug which is in the form of a salt, such as an antihistamine, guaifenesin, codeine, or dihydrocodeine, or hydrocodone can be incorporated as an ion-exchange resin complex.

Procedure:
(1) Add the appropriate amount of sodium polystyrene sulphonate USP (e.g. Amberlite® IRP 69) to a phenylepherine hydrochloride solution.
(2) Stir the mix for 12 hrs to allow complete drug/resin complex formation.
(3) Separate and dry the insoluble drug/resin complex.
(4) Granulate the drug/resin complex with a delayed release/enteric polymer (e.g. Eudragit® L 100, Kollidon® MAE, Aquacoat® cPD) and dry the granules.
(5) Mill the granules, if needed.
(6) To the milled granules add the appropriate amount of microcrystalline cellulose and the remaining phenylepherine hydrochloride or a pharmaceutically acceptable salt thereof in a V shaped blender and mix for 15 minutes.
(7) Add prescreened (sieve #30) magnesium stearate to the above blend and mix for 3 minutes.
(8) Fill into appropriate capsules.

Example 20

Extended Release Suspension (Gel)

An extended release suspension (in the form of a gel) in accordance with the present invention which contains a phenylepherine hydrochloride ion-exchange complex and promethazine hydrochloride is illustrated as follows (the phenylepherine hydrochloride is used in a controlled release form since it has a shorter half-life than the promethazine hydrochloride):

| Ingredients | Amount/5 ml |
| --- | --- |
| Phenylepherine hydrochloride Ion-Exchange Complex | Equivalent to 30 mg of Phenylepherine |
| Promethazine HCl | 25 mg |
| Eudragit ® L 100 | 0.2 to 2.8 g |
| Glycerin | 315 mg |
| Polysorbate 80 | 1.5 mg |
| Carbomer (e.g., Carbopol ® 974) | 37.5 mg |
| Methyl Paraben | 9 mg |
| Propyl Paraben | 1 mg |
| Saccharin Sodium cryst., USP | 0.1 mg |
| Artificial Grape Flavor | 5 mg |
| FD&C Red # 40 Dye | 0.5 mg |
| Sodium Hydroxide | to pH of 6.5 |
| Water | to 5 ml |

Procedure:
(1) Add the appropriate amount of sodium polystyrene sulphonate USP (e.g. Amberlite® IRP 69) to a phenylepherine hydrochloride solution.
(2) Stir the mix for 12 hrs to allow complete drug/resin complex formation.
(3) Separate and dry the insoluble drug/resin complex.
(4) Granulate the drug/resin complex with a delayed release/enteric polymer (e.g. Eudragit® L 100, Kollidon® MAE, Aquacoat® cPD) and dry the granules.
(5) Mill the granules, if needed.
(6) To an appropriate amount of water add the following ingredients and dissolve: promethazine hydrochloride, Carbomer (e.g., Carbopol® 974), glycerin, polysorbate 80, methyl paraben, propyl paraben, artificial grape flavor, FD&C red #40 dye.
(7) Add milled granules.
(8) Add water to 80% of final volume.
(9) Agitate at suitable rate to avoid settling of the suspension and maintain a homogeneous product mixture.
(10) Neutralize the solution to a pH of 6.5 (range 5.5 to 7.5) to form a gel using a IN sodium hydroxide solution. QS with water to make final volume of 5 ml per dose.
(11) Fill in suitable containers.

Example 21

Extended Release Suspension (Liquid)

An extended release suspension (in the form of a liquid) in accordance with the present invention which contains a phenylepherine hydrochloride ion-exchange complex and promethazine hydrochloride is illustrated as follows:

| Ingredients | Amount/5 ml |
|---|---|
| Phenylepherine hydrochloride Ion-Exchange Complex | Equivalent to 45 mg of Phenylepherine hydrochloride |
| Promethazine HCl | 25 mg |
| Eudragit ® L 100 | 0.2 to 2.8 g |
| Silica, colloidal anhydrous, NF | 100 mg |
| Glycerin | 740 mg |
| Xylitol, NF | 800 mg |
| Sodium Citrate, USP | 100 mg |
| Saccharin Sodium cryst., USP, | 0.1 mg |
| Sodium Benzoate | 7.5 mg |
| Citric Acid Monohydrate, USP | 8.0 mg |
| Artificial Grape Flavor | 5 mg |
| FD&C Red # 40 Dye | 0.5 mg |
| Water | q.s to 5 ml |

Manufacturing Process for 1000 L Batch:

Add the appropriate amount of sodium polystyrene sulphonate USP (e.g. Amberlite® IRP 69) to a phenylepherine hydrochloride solution. Stir the mix for 12 hrs to allow complete drug/resin complex formation. Separate and dry the insoluble drug/resin complex. Granulate the drug/resin complex with a delayed release/enteric polymer (e.g. Eudragit® L 100, Kollidon® MAE, Aquacoat® CPD) and dry the granules. Mill the granules, if needed.

In a suitably sized stainless steel vessel, dissolve saccharin sodium, sodium benzoate, citric acid, and sodium citrate in approximately 50 L of warm (about 45° C.), purified water. In another large stainless steel drum mix the silica, phenylepherine hydrochloride ion-exchange complex, and promethazine hydrochloride until a uniform and consistent mixture is obtained. In a separate 1000 L stainless steel tank equipped with a suitably sized homogenizer/disperser add about 100 L of purified water. With the homogenizer on, add the silica mixture containing phenylepherine hydrochloride ion-exchange complex, and promethazine hydrochloride. Add the previously prepared solution of saccharin sodium, sodium benzoate, citric acid, and sodium citrate to the 1000 L tank. Rinse the first vessel with about 2 L of water and transfer the rinsate to the 1000 L tank. Add the remaining ingredients and homogenize for 15 minutes.

Example 22

Extended Release Suspension (Liquid)

An extended release suspension (in the form of a liquid) in accordance with the present invention which contains a codeine phosphate ion-exchange complex, phenylepherine tannate and chlorpheniramine tannate is illustrated as follows:

| Ingredients | Amount/5 ml |
|---|---|
| Codeine phosphate Ion-exchange complex | Equivalent to 45 mg Codeine phosphate |
| Phenylepherine Tannate | 75.0 |
| Chlorpheniramine Tannate | 4.5 |
| Eudragit ® L 100 | 0.2 to 2.8 grams |
| Silica, colloidal anhydrous, NF | 100 mg |
| Glycerin | 740 mg |
| Xylitol, NF | 800 mg |
| Sodium Citrate, USP | 100 mg |
| Saccharin Sodium cryst., USP, | 0.1 mg |

-continued

| Ingredients | Amount/5 ml |
|---|---|
| Sodium Benzoate | 7.5 mg |
| Citric Acid Monohydrate, USP | 8.0 mg |
| Artificial Grape Flavor | 5 mg |
| FD&C Red # 40 Dye | 0.5 mg |
| Water | q.s to 5 ml |

Manufacturing Process for 1000 Kg Batch:

Add the appropriate amount of sodium polystyrene sulphonate USP (e.g. Amberlite® IRP 69) to a codeine phosphate solution. Stir the mix for 12 hrs to allow complete drug/resin complex formation. Separate and dry the insoluble drug/resin complex. Granulate the drug/resin complex with a delayed release/enteric polymer (e.g. Eudragit® L 100, Kollidon® MAE, Aquacoat® CPD) and dry the granules. Mill the granules, if needed.

In a suitably sized stainless steel vessel, dissolve saccharin sodium, sodium benzoate, citric acid, and sodium citrate in approximately 50 L of warm (about 45° C.), purified water. In another large stainless steel drum mix the silica and the codeine phosphate ion-exchange complex, phenylepherine tannate, and the chlorpheniramine tannate until a uniform and consistent mixture is obtained. In a separate 1000 L stainless steel tank equipped with a suitably sized homogenizer/disperser add about 100 L of purified water. With the homogenizer on, add the silica mixture containing the codeine phosphate ion-exchange complex, the phenylepherine tannate, and the chlorpheniramine tannate. Add the previously prepared solution of saccharin sodium, sodium benzoate, citric acid, and sodium citrate to the 1000 L tank. Rinse the first vessel with about 2 L of water and transfer the rinse to the 1000 L tank. Add the remaining ingredients and homogenize for 15 minutes.

Reference Example 1

Extended Release Suspension

An extended release suspension which contains a hydrocodone bitartrate ion-exchange complex, a dexchlorpheniramine maleate ion-exchange complex and a phenylepherine hydrochloride ion-exchange complex is illustrated as follows:

| Ingredients | Amount/5 ml |
|---|---|
| Hydrocodone Bitartrate Ion-Exchange Complex | Equivalent to 8 mg of Hydrocodone bitartrate |
| Dexchlorpheniramine Maleate Ion-Exchange Complex | Equivalent to 6 mg of Dexchlorpheniramine Maleate |
| Phenylepherine HCl Ion-Exchange Complex | Equivalent to 10 mg of Phenylepherine HCl |
| Eudragit ® L 100 | 0.2 to 2.8 g |
| Glycerin | 315 mg |
| Polysorbate 80 | 1.5 mg |
| Carbomer (e.g., Carbopol ® 974) | 15 mg |
| Methyl Paraben | 9 mg |
| Propyl Paraben | 1 mg |
| Artificial Grape Flavor | 5 mg |
| FD&C Red # 40 Dye | 0.5 mg |
| Water | q.s |

The formula described above serves as a non-limiting example. Any active drug which is in the form of a salt, such as an antihistamine, codeine, or dihydrocodeine, can be incorporated as an ion-exchange resin complex.

Procedure:
(1) Add the appropriate amount of sodium polystyrene sulphonate USP (e.g. Amberlite® IRP 69) to a dexchlorpheniramine maleate, hydrocodone bitartrate and phenylepherine HCl solution.
(2) Stir the mix for 12 hrs to allow complete drug/resin complex formation.
(3) Separate and dry the insoluble drug/resin complex.
(4) Granulate the drug/resin complex with a delayed release/enteric polymer (e.g. Eugragit® L 100, Kollidon® MAE, Aquacoa®t cPD) and dry the granules.
(5) Mill the granules, if needed.
(6) To an appropriate amount of water add the following ingredients and dissolve: Carbomer (e.g., Carbopol® 974), glycerin, polysorbate 80, methyl paraben, propyl paraben, artificial grape flavor, FD&C red #40 dye.
(7) Add milled granules.
(8) Add water to make up to a final volume.
(9) Agitate at suitable rate to avoid settling of the suspension and maintain a homogeneous product mixture.
(10) Fill in suitable containers ensuring that the product is homogeneous throughout the filling operation.

Reference Example 2

Suspension Formula

A suspension formula which comprises codeine phosphate and phenylepherine tannate is illustrated as follows:

| Ingredients | g/100 mL | kg/batch |
|---|---|---|
| Codeine Phosphate | 0.20 | 1.667 |
| Phenylepherine Tannate | 0.80 | 6.667 |
| Silica, colloidal anhydrous, NF | 1.73 | 14.417 |
| Hydroxyethylcellulose, NF | 0.05 | 0.417 |
| Sorbitol Solution 70% (non-crystallizing), NF | 34.00 | 283.333 |
| Glycerol | 14.75 | 122.917 |
| Xylitol, NF | 16.00 | 133.333 |
| Sodium Citrate, USP | 2.00 | 16.667 |
| Saccharin Sodium cryst., USP, | 0.01 | 0.083 |
| Sodium Benzoate, NF | 0.15 | 1.250 |
| Citric Acid Monohydrate, USP | 0.16 | 1.333 |
| Strawberry Flavor | 0.15 | 1.250 |
| Banana Flavor | 0.15 | 1.250 |
| Purified Water | 49.55 | 412.917 |
| Total Amount | 120.00 | 1000.000 |

Manufacturing Process for 1000 kg Batch:
In a suitably sized stainless steel vessel, dissolve saccharin sodium, sodium benzoate, citric acid, and sodium citrate in approximately 50 L of warm (about 45° C.), purified water. In another large stainless steel drum mix the silica, codeine phosphate and micronized phenylepherine tannate until a uniform and consistent mixture is obtained. In a separate 1000 L stainless steel tank equipped with a suitably sized homogenizer/disperser add about 100 L of purified water. With the homogenizer on, add the silica mixture containing phenylepherine tannate and codeine phosphate Add the previously prepared solution of saccharin sodium, sodium benzoate, citric acid, and sodium citrate to the 1000 L tank. Rinse the first vessel with about 2 L of water and transfer the rinse to the 1000 L tank. Add the remaining ingredients and homogenize for 15 minutes. Filter product through a 10 micron filter and fill in appropriately sized containers.
To make products with other agents such as antihistamines, decongestants, or expectorants, one or more combinations of each of the ingredients in a range as described in Table 1 below can be made depending on the specific therapeutic effect desired.

Reference Example 3

Liquid Formula

A liquid dosage form which comprises phenylepherine hydrochloride is illustrated as follows:

| Ingredients | Per 5 mL | Per 425 L |
|---|---|---|
| Codeine Phosphate USP | 30 mg | 2.550 kg |
| Phenylepherine Hydrochloride USP | 10.0 mg | 0.850 kg |
| Methyl Paraben USP | 9.0 mg | 0.765 kg |
| Propyl Paraben USP | 1.0 mg | 0.085 kg |
| Propylene Glycol USP | 259 mg | 22.016 kg |
| Saccharin Sodium USP | 3.18 mg | 0.270 kg |
| Citric Acid USP | 5.0 mg | 0.425 kg |
| Strawberry Flavor | 10 mg | 0.850 kg |
| Banana Flavor | 10 mg | 0.850 kg |
| Sorbitol Solution 70% USP | 3212.5 mg | 273.1 kg |
| Purified Water, as required to q.s. to | 5.0 mL | 425 L |

Manufacturing Process for 425 L Batch Size:
In a suitably sized stainless steel vessel, dissolve methyl paraben and propyl paraben in approximately 50 L of warm (about 45° C.), purified water. Add about half of the propylene glycol and mix for about 1 hr. In a separate 1000 L stainless steel tank equipped with a suitably sized agitator, add about 50 L of purified water. With the agitator on, add phenylepherine hydrochloride, codeine phosphate, saccharin sodium and citric acid and dissolve. Add the previously prepared paraben/propylene glycol solution to the 1000 L tank. Rinse the first vessel with about 2 L of water and transfer the rinsate to the 1000 L tank. Add the remaining propylene glycol to a suitably sized stainless steel vessel and dissolve the strawberry and banana flavors. Transfer this to the 1000 L tank. Rinse the container with 2 L of purified water and transfer to the 1000 L tank. With the agitator on, add the sorbitol solution 70% to the 1000 L tank. In a suitably sized stainless steel vessel, dissolve the codeine phosphate in about 5 L of purified water and transfer to the 1000 L tank. Rinse the container with about 2 L of purified water and transfer to the 1000 L tank. Stop the agitator and let the solution stand for 15 minutes. QS to 425 L with purified water. Filter product through a 1 micron filter and fill in appropriately sized containers.
To make products with other antihistamines, decongestants, or expectorants, one or more combinations of each of the ingredients in a range as described in Table 1 above can be made depending on the specific therapeutic effect desired.
It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A pharmaceutical dosage form, wherein the pharmaceutical dosage form comprises (a) phenylepherine or a pharmaceutically acceptable salt thereof in a first form or layer and (b) phenylepherine or a pharmaceutically acceptable salt thereof in a second form or layer which is different from the first form or layer, the first form or layer being a controlled release form or layer and the second form or layer being a controlled release form or layer that is different from the first form or layer and the dosage form releasing the phenylepherine (b) over a different period and at a different rate than the phenylepherine (a).

2. The dosage form of claim 1, wherein the dosage form comprises phenylepherine hydrochloride.

3. The dosage form of claim 1, wherein the dosage form comprises phenylepherine tannate.

4. The dosage form of claim 1, wherein the dosage form is a bi-layered tablet and at least one of the layers comprises an additional drug.

5. The dosage form of claim 4, wherein the dosage form comprises phenylepherine hydrochloride.

6. The dosage form of claim 4, wherein the dosage form comprises phenylepherine tannate.

7. The dosage form of claim 4, wherein the at least one additional drug is selected from antitussives, expectorants, mucus thinning drugs, analgesics and antihistamines.

8. The dosage form of claim 4, wherein the at least one additional drug comprises an antitussive drug.

9. The dosage form of claim 8, wherein the at least one additional drug comprises at least one drug selected from codeine, hydrocodone, dihydrocodeine, carbetapentane, and pharmaceutically acceptable salts thereof.

10. The dosage form of claim 8, wherein the at least one additional drug comprises codeine phosphate.

11. The dosage form of claim 8, wherein the at least one additional drug comprises hydrocodone bitartrate.

12. The dosage form of claim 8, wherein the at least one additional drug comprises dihydrocodeine bitartrate.

13. The dosage form of claim 8, wherein the at least one additional drug comprises carbetapentane citrate.

14. The dosage form of claim 4, wherein the at least one additional drug comprises dextromethorphan hydrobromide.

15. The dosage form of claim 4, wherein the at least one additional drug comprises at least one antihistamine.

16. The dosage form of claim 15, wherein the at least one antihistamine comprises at least one compound selected from astemizole, zatadine, bromodiphenhydramine, brompheniramine, carbinoxamine, cetirizine, chlorcyclizine, clemastine, chlorothen, chlorpheniramine, cyclizine, cyproheptadine, desloratadine, dimethindene, diphenhydramine, diphenylpyraline, doxylamine, fexofenadine, hydroxyine, isothipendyl, loratadine, methapyrilene, montelukast, phenindamine, pheniramine, phenyltoloxamine, promethazine, prophpyridamine, pyrilamine, terfenadine, thenyldiamine, thonzylamine, trimeprazine, tripelennamine, triprolidine, and pharmaceutically acceptable salts thereof.

17. The dosage form of claim 15, wherein the at least one antihistamine comprises at least one of astemizole, zatadine maleate, bromodiphenhydramine HCl, brompheniramine maleate, carbinoxamine maleate, cetirizine HCl, chlorcyclizine HCl, clemastine fumarate, chlorothen citrate, chlorpheniramine maleate, cyclizine, cyproheptadine, desloratadine, dimethindene maleate, diphenhydramine HCl, diphenylpyraline, doxylamine, fexofenadine HCl, hydroxyine HCl, isothipendyl HCl (theruhistin), loratadine, methapyrilene fumarate, methapyrilene HCl, montelukast sodium, phenindamine tartrate, pheniramine maleate, phenyltoloxamine citrate, promethazine hydrochloride, prophenpyridamine maleate, pyrilamine maleate, terfenadine, thenyldiamine HCl, thonzylamine, trimeprazine tartrate, tripelennamine HCl and triprolidine HCl.

18. The dosage form of claim 15, wherein the at least one antihistamine comprises promethazine hydrochloride.

19. The dosage form of claim 15, wherein the at least one antihistamine comprises brompheniramine maleate.

20. The dosage form of claim 15, wherein the at least one antihistamine comprises chlorpheniramine maleate.

21. The dosage form of claim 15, wherein the at least one antihistamine comprises diphenhydramine HCl.

22. The dosage form of claim 4, wherein the at least one additional drug comprises an expectorant.

23. The dosage form of claim 22, wherein the expectorant comprises guaifenesin.

24. The dosage form of claim 4, wherein a plasma half-life of the at least one additional drug differs from a plasma half-life of phenylepherine by at least about 2 hours.

25. The dosage form of claim 4, wherein a plasma half-life of the at least one additional drug differs from a plasma half-life of phenylepherine by at least about 3 hours.

26. The dosage form of claim 4, wherein a plasma half-life of the at least one second drug differs from a plasma half-life of phenylepherine by at least about 4 hours.

27. The dosage form of claim 1, wherein the dosage form releases phenylepherine or a pharmaceutically acceptable salt thereof independently over a first period and over a second period and not more than about 30% of the second period is coextensive with all or a part of the first period.

28. The dosage form of claim 27, wherein there is substantially no overlap between the first and second periods.

29. A pharmaceutical dosage form, wherein the dosage form is a bi-layered tablet which comprises two different controlled release forms or layers of at least one of phenylepherine and a pharmaceutically acceptable salt thereof and comprises at least about 37 mg of phenylepherine or an equivalent amount of a pharmaceutically acceptable salt thereof.

30. The dosage form of claim 29, wherein the dosage form comprises at least about 40 mg of phenylepherine or an equivalent amount of a pharmaceutically acceptable salt thereof.

31. The dosage form of claim 29, wherein the dosage form comprises at least about 45 mg of phenylepherine or an equivalent amount of a pharmaceutically acceptable salt thereof.

32. The dosage form of claim 29, wherein the dosage form comprises at least about 50 mg of phenylepherine or an equivalent amount of a pharmaceutically acceptable salt thereof.

33. The dosage form of claim 29, wherein the dosage form comprises phenylepherine hydrochloride.

34. The dosage form of claim 29, wherein the dosage form comprises phenylepherine tannate.

35. The dosage form of claim 29, wherein the dosage form comprises at least one additional drug.

36. The dosage form of claim 35, wherein the dosage form comprises phenylepherine hydrochloride.

37. The dosage form of claim 35, wherein the dosage form comprises phenylepherine tannate.

38. The dosage form of claim 35, wherein the at least one additional drug comprises at least one of an expectorant, a mucus thinning drug, an antihistamine, an antitussive drug and an analgesic.

39. The dosage form of claim 35, wherein the at least one additional drug comprises an antitussive drug.

40. The dosage form of claim 39, wherein the at least one additional drug comprises at least one drug selected from codeine, hydrocodone, dihydrocodeine, carbetapentane, and pharmaceutically acceptable salts thereof.

41. The dosage form of claim 39, wherein the at least one additional drug comprises codeine phosphate.

42. The dosage form of claim 39, wherein the at least one additional drug comprises hydrocodone bitartrate.

43. The dosage form of claim 39, wherein the at least one additional drug comprises dihydrocodeine bitartrate.

44. The dosage form of claim 39, wherein the at least one additional drug comprises carbetapentane citrate.

45. The dosage form of claim 35, wherein the at least one additional drug comprises dextromethorphan hydrobromide.

46. The dosage form of claim 35, wherein the at least one additional drug comprises at least one antihistamine.

47. The dosage form of claim 46, wherein the at least one antihistamine comprises at least one compound selected from astemizole, zatadine, bromodiphenhydramine, brompheniramine, carbinoxamine, cetirizine, chlorcyclizine, clemastine, chlorothen, chlorpheniramine, cyclizine, cyproheptadine, desloratadine, dimethindene, diphenhydramine, diphenylpyraline, doxylamine, fexofenadine, hydroxyine, isothipendyl, loratadine, methapyrilene, montelukast, phenindamine, pheniramine, phenyltoloxamine, promethazine, prophenpyridamine, pyrilamine, terfenadine, thenyldiamine, thonzylamine, trimeprazine, tripelennamine, triprolidine, and pharmaceutically acceptable salts thereof.

48. The dosage form of claim 46, wherein the at least one antihistamine comprises at least one of astemizole, zatadine maleate, bromodiphenhydramine HCl, brompheniramine maleate, carbinoxamine maleate, cetirizine HCl, chlorcyclizine HCl, clemastine fumarate, chlorothen citrate, chlorpheniramine maleate, cyclizine, cyproheptadine, desloratadine, dimethindene maleate, diphenhydramine HCl, diphenylpyraline, doxylamine, fexofenadine HCl, hydroxyine HCl, isothipendyl HCl (theruhistin), loratadine, methapyrilene fumarate, methapyrilene HCl, montelukast sodium, phenindamine tartrate, pheniramine maleate, phenyltoloxamine citrate, promethazine hydrochloride, prophenpyridamine maleate, pyrilamine maleate, terfenadine, thenyldiamine HCl, thonzylamine, trimeprazine tartrate, tripelennamine HCl and triprolidine HCl.

49. The dosage form of claim 46, wherein the at least one antihistamine comprises promethazine hydrochloride.

50. The dosage form of claim 46, wherein the at least one antihistamine comprises brompheniramine maleate.

51. The dosage form of claim 46, wherein the at least one antihistamine comprises chlorpheniramine maleate.

52. The dosage form of claim 46, wherein the at least one antihistamine comprises diphenhydramine HCl.

53. The dosage form of claim 35, wherein the at least one additional drug comprises an expectorant.

54. The dosage form of claim 53, wherein the expectorant comprises guaifenesin.

55. The dosage form of claim 35, wherein a plasma half-life of the at least one additional drug differs from a plasma half-life of phenylepherine by at least about 2 hours.

56. The dosage form of claim 35, wherein a plasma half-life of the at least one additional drug differs from a plasma half-life of phenylepherine by at least about 3 hours.

57. The dosage form of claim 35, wherein a plasma half-life of the at least one second drug differs from a plasma half-life of phenylepherine by at least about 4 hours.

58. The dosage form of claim 29, wherein the dosage form releases phenylepherine or a pharmaceutically acceptable salt thereof independently over a first period and over a second period and not more than about 30% of the second period is coextensive with all or a part of the first period.

59. The dosage form of claim 58, wherein there is substantially no overlap between the first and second periods.

60. The dosage form of claim 31, wherein the dosage form comprises at least one additional drug.

61. The dosage form of claim 60, wherein the at least one additional drug comprises at least one of an expectorant, a mucus thinning drug, an antihistamine, an antitussive drug and an analgesic.

62. The dosage form of claim 60, wherein the at least one additional drug comprises an antitussive drug.

63. The dosage form of claim 62, wherein the at least one additional drug comprises at least one drug selected from codeine, hydrocodone, dihydrocodeine, carbetapentane, and pharmaceutically acceptable salts thereof.

64. The dosage form of claim 62, wherein the at least one additional drug comprises codeine phosphate.

65. The dosage form of claim 62, wherein the at least one additional drug comprises hydrocodone bitartrate.

66. The dosage form of claim 62, wherein the at least one additional drug comprises dihydrocodeine bitartrate.

67. The dosage form of claim 62, wherein the at least one additional drug comprises carbetapentane citrate.

68. The dosage form of claim 60, wherein the at least one additional drug comprises dextromethorphan hydrobromide.

69. The dosage form of claim 60, wherein the at least one additional drug comprises at least one antihistamine.

70. The dosage form of claim 69, wherein the at least one antihistamine comprises at least one compound selected from astemizole, zatadine, bromodiphenhydramine, brompheniramine, carbinoxamine, cetirizine, chlorcyclizine, clemastine, chlorothen, chlorpheniramine, cyclizine, cyproheptadine, desloratadine, dimethindene, diphenhydramine, diphenylpyraline, doxylamine, fexofenadine, hydroxyine, isothipendyl, loratadine, methapyrilene, montelukast, phenindamine, pheniramine, phenyltoloxamine, promethazine, prophenpyridamine, pyrilamine, terfenadine, thenyldiamine, thonzylamine, trimeprazine, tripelennamine, triprolidine, and pharmaceutically acceptable salts thereof.

71. The dosage form of claim 69, wherein the at least one antihistamine comprises at least one of astemizole, zatadine maleate, bromodiphenhydramine HCl, brompheniramine maleate, carbinoxamine maleate, cetirizine HCl, chlorcyclizine HCl, clemastine fumarate, chlorothen citrate, chlorpheniramine maleate, cyclizine, cyproheptadine, desloratadine, dimethindene maleate, diphenhydramine HCl, diphenylpyraline, doxylamine, fexofenadine HCl, hydroxyine HCl, isothipendyl HCl (theruhistin), loratadine, methapyrilene fumarate, methapyrilene HCl, montelukast sodium, phenindamine tartrate, pheniramine maleate, phenyltoloxamine citrate, promethazine hydrochloride, prophenpyridamine maleate, pyrilamine maleate, terfenadine, thenyldiamine HCl, thonzylamine, trimeprazine tartrate, tripelennamine HCl and triprolidine HCl.

72. The dosage form of claim 69, wherein the at least one antihistamine comprises promethazine hydrochloride.

73. The dosage form of claim 69, wherein the at least one antihistamine comprises brompheniramine maleate.

74. The dosage form of claim 69, wherein the at least one antihistamine comprises chlorpheniramine maleate.

75. The dosage form of claim 69, wherein the at least one antihistamine comprises diphenhydramine HCl.

76. The dosage form of claim 60, wherein the at least one additional drug comprises an expectorant.

77. The dosage form of claim 76, wherein the expectorant comprises guaifenesin.

78. The dosage form of claim 60, wherein a plasma half-life of the at least one additional drug differs from a plasma half-life of phenylepherine by at least about 2 hours.

79. The dosage form of claim 60, wherein a plasma half-life of the at least one additional drug differs from a plasma half-life of phenylepherine by at least about 3 hours.

80. The dosage form of claim 60, wherein a plasma half-life of the at least one second drug differs from a plasma half-life of phenylepherine by at least about 4 hours.

81. The dosage form of claim 30, wherein the dosage form releases phenylepherine or a pharmaceutically acceptable salt thereof independently over a first period and over a second period and not more than about 30% of the second period is coextensive with all or a part of the first period.

82. The dosage form of claim 81, wherein there is substantially no overlap between the first and second periods.

83. The dosage form of claim 30, wherein the dosage form comprises phenylepherine hydrochloride.

84. The dosage form of claim 30, wherein the dosage form comprises phenylepherine tannate.

85. The dosage form of claim 31, wherein the dosage form releases phenylepherine or a pharmaceutically acceptable salt thereof independently over a first period and over a second period and not more than about 30% of the second period is coextensive with all or a part of the first period.

86. The dosage form of claim 85, wherein there is substantially no overlap between the first and second periods.

87. The dosage form of claim 31, wherein the dosage form comprises phenylepherine hydrochloride.

88. The dosage form of claim 31, wherein the dosage form comprises phenylepherine tannate.

89. The dosage form of claim 32, wherein the dosage form releases phenylepherine or a pharmaceutically acceptable salt thereof independently over a first period and over a second period and not more than about 30% of the second period is coextensive with all or a part of the first period.

90. The dosage form of claim 89, wherein there is substantially no overlap between the first and second periods.

91. The dosage form of claim 32, wherein the dosage form comprises phenylepherine hydrochloride.

92. The dosage form of claim 32, wherein the dosage form comprises phenylepherine tannate.

93. The dosage form of claim 30, wherein the dosage form comprises at least one additional drug.

94. The dosage form of claim 93, wherein the dosage form comprises phenylepherine hydrochloride.

95. The dosage form of claim 93, wherein the dosage form comprises phenylepherine tannate.

96. The dosage form of claim 93, wherein the at least one additional drug comprises at least one of an expectorant, a mucus thinning drug, an antihistamine, an antitussive drug and an analgesic.

97. The dosage form of claim 96, wherein the at least one additional drug comprises at least one drug selected from codeine, hydrocodone, dihydrocodeine, carbetapentane, and pharmaceutically acceptable salts thereof.

98. The dosage form of claim 96, wherein the at least one additional drug comprises at least one antihistamine.

99. The dosage form of claim 96, wherein the at least one additional drug comprises an expectorant.

100. The dosage form of claim 96, wherein a plasma half-life of the at least one additional drug differs from a plasma half-life of phenylepherine by at least about 2 hours.

101. The dosage form of claim 96, wherein a plasma half-life of the at least one additional drug differs from a plasma half-life of phenylepherine by at least about 3 hours.

102. The dosage form of claim 96, wherein a plasma half-life of the at least one second drug differs from a plasma half-life of phenylepherine by at least about 4 hours.

103. The dosage form of claim 32, wherein the dosage form comprises at least one additional drug.

104. The dosage form of claim 103, wherein the dosage form comprises phenylepherine hydrochloride.

105. The dosage form of claim 103, wherein the dosage form comprises phenylepherine tannate.

106. The dosage form of claim 103, wherein the at least one additional drug comprises at least one of an expectorant, a mucus thinning drug, an antihistamine, an antitussive drug and an analgesic.

107. The dosage form of claim 106, wherein the at least one additional drug comprises at least one drug selected from codeine, hydrocodone, dihydrocodeine, carbetapentane, and pharmaceutically acceptable salts thereof.

108. The dosage form of claim 106, wherein the at least one additional drug comprises at least one antihistamine.

109. The dosage form of claim 106, wherein the at least one additional drug comprises an expectorant.

110. The dosage form of claim 106, wherein a plasma half-life of the at least one additional drug differs from a plasma half-life of phenylepherine by at least about 2 hours.

111. The dosage form of claim 106, wherein a plasma half-life of the at least one additional drug differs from a plasma half-life of phenylepherine by at least about 3 hours.

112. The dosage form of claim 106, wherein a plasma half-life of the at least one second drug differs from a plasma half-life of phenylepherine by at least about 4 hours.

* * * * *